(12) United States Patent  
Dussault et al.

(10) Patent No.: US 9,829,487 B2  
(45) Date of Patent: *Nov. 28, 2017

(54) SELF-ASSEMBLED MONOLAYERS AND METHODS FOR USING THE SAME IN BIOSENSING APPLICATIONS

(71) Applicant: NUtech Ventures, Lincoln, NE (US)

(72) Inventors: Patrick H. Dussault, Lincoln, NE (US); Rebecca Y. Lai, Lincoln, NE (US); Thomas Fisher, Lincoln, NE (US); Anita J. Zaitouna, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/798,145

(22) Filed: Jul. 13, 2015

(65) Prior Publication Data

US 2016/0047803 A1    Feb. 18, 2016

Related U.S. Application Data

(63) Continuation of application No. 13/491,168, filed on Jun. 7, 2012, now Pat. No. 9,079,835.

(60) Provisional application No. 61/622,727, filed on Apr. 11, 2012, provisional application No. 61/494,026, filed on Jun. 7, 2011.

(51) Int. Cl.
| | |
|---|---|
| *G01N 33/53* | (2006.01) |
| *C07C 323/16* | (2006.01) |
| *C07C 323/12* | (2006.01) |
| *G01N 33/543* | (2006.01) |
| *C07C 323/14* | (2006.01) |
| *C07C 327/28* | (2006.01) |

(52) U.S. Cl.
CPC ..... *G01N 33/54393* (2013.01); *C07C 323/12* (2013.01); *C07C 323/14* (2013.01); *C07C 323/16* (2013.01); *C07C 327/28* (2013.01); *G01N 33/54353* (2013.01); *G01N 2333/161* (2013.01); *G01N 2333/415* (2013.01); *G01N 2610/00* (2013.01)

(58) Field of Classification Search
CPC ... C07C 323/12; C07C 323/14; C07C 323/16; C07C 327/28; G01N 33/54353; G01N 33/54393; G01N 2610/00; G01N 2333/161; G01N 2333/415
See application file for complete search history.

(56) References Cited

U.S. PATENT DOCUMENTS 9,079,835 B2    7/2015 Dussault et al.

OTHER PUBLICATIONS

Sigal et al. A self-assembled monolayer ofr the binding and study of histidine-tagged proteins by surface plasmon resonance. Anal. Chem. 1996, vol. 68, pp. 490-497.*

James E. Redman. Ph.D. Thesis, University of Cambridge, 2000, pp. 1-9.*

(Continued)

*Primary Examiner* — Shafiqul Haq  
(74) *Attorney, Agent, or Firm* — Fish & Richardson P.C.

(57) ABSTRACT

Cross-linked amphiphile constructs that form self-assembled monolayers (SAMs) on metal surfaces such as gold surfaces are disclosed. These new SAMs generate well packed and highly oriented monolayer films on gold surfaces. A method for using the SAMs in the fabrication of biomolecule sensors is also disclosed.

28 Claims, 10 Drawing Sheets

(56) References Cited

OTHER PUBLICATIONS

Zaitouna et al. Design and characterization of a metal ion-imidazole self-assembled monolayer for reversible immobilization of histidine-tagged peptides. Chem. Commun. 2011, vol. 47, pp. 12391-12393.*
Andersson et al., "Coordination of Imidazoles by Cu(II) and Zn(II) as Studied by NMR Relaxometry, EPR, far-FTIR Vibrational Spectroscopy and Ab Initio Calculations: Effect of Methyl Substitution," *J. Phys. Chem. A*, 2010, 114:13146-13153.
Auffinger and Hashem, "Nucleic acid solvation: from outside to insight," *Curr Opin Structural Biol.*, 2007, 17:325-333.
Baker et al., "An Electronic, Aptamer-Based Small-Molecule Sensor for the Rapid, Label-Free Detection of Cocaine in Adulterated Samples and Biological Fluids," *J Am. Chem. Soc.*, 2006, 128:3138-3139.
Balland et al., "Characterization of the Electron Transfer of a Ferrocene Redox Probe and a Histidine-Tagged Hemoprotein Specifically Bound to a Nitrilotriacetic-Terminated Self-Assembled Monolayer," *Langmuir*, 2009, 25:6532-6542.
Boubour and Lennox, "Insulating Properties of Self-Assembled Monolayers Monitored by Impedance Spectroscopy," *Langmuir*, 2000, 16:4222-4228.
Cañete et al., "Folding-based electrochemical DNA sensor fabricated by "click" chemistry," *Chem. Commun.*, 2009, 4835-4837.
Cash et al., "Optimization of a Reusable, DNA Pseudoknot-Based Electrochemical Sensor for Sequence-Specific DNA Detection in Blood Serum," *Anal. Chem.*, 2009, 81:656-661.
Chaga, "Twenty-five years of immobilized metal ion affinity chromatography: past, present and future," *J. Biochem. Biophys. Methods*, 2001, 49:313-334.
Chan and Yousaf, "Site-Selective Immobilization of Ligands with Control of Density on Electroactive Microelectrode Arrays," *ChemPhysChem*, 2007, 8:1469-1472.
Chan et al., "Polytriazoles as Copper(I)-Stabilizing Ligands in Catalysis," *Org. Lett.*, 2004, 6:2853-2855.
Collman et al., "'Clicking' Functionality onto Electrode Surfaces," *Langmuir*, 2004, 20:1051-1053.
Collman et al., "Mixed Azide-Terminated Monolayers: A Platform for Modifying Electrode Surfaces," *Langmuir*, 2006, 22:2457-2464.
Devaraj et al., "Chemoselective Covalent Coupling of Oligonucleotide Probes to Self-Assembled Monolayers," *J. Am. Chem. Soc.*, 2005, 127:8600-8601.
Devaraj et al., "Selective Functionalization of Independently Addressed Microelectrodes by Electrochemical Activation and Deactivation of a Coupling Catalyst," *J Am. Chem. Soc.*, 2006, 128:1794-1795.
Donnelly et al., "'Click' cycloaddition catalysts: copper(I) and copper(II) tris(triazolylmethyl)amine complexes," *Chem. Commun.*, 2008, 2459-2461.
Drummond et al., "Electrochemical DNA sensors," *Nat. Biotechnol.*, 2003, 21:1192-1199.
Duguid and Bloomfield, "Aggregation of melted DNA by divalent metal ion-mediated cross-linking," *Biophysical J.*, 1995, 69:2642-2648.
Fan et al., "Electrochemical interrogation of conformational changes as a reagentless method for the sequence-specific detection of DNA," *Proc. Natl. Acad. Sci.*, 2003, 100:9134-9137.
Fisher et al., "Design and Synthesis of a c Class of Twin-Chain Amphiphiles for Self-Assembled Monolayer-Based Electrochemical Biosensor Applications," European Journal of Organic Chemistry, 2012, 3623-3270.
Fragoso et al., "Electron permeable self-assembled monolayers of dithiolated aromatic scaffolds on gold for biosensor applications," *Anal. Chem.*, 2008, 80: 2556-2563.
Gaberc-Porekar and V. Menart, "Perspectives of immobilized-metal affinity chromatography," *J. Biochem. Biophys. Methods*, 2001, 49:335-360.
Garg et al, "Self-assembled monolayers composed of aromatic thiols on gold: structural characterization and thermal stability in solution," *Langmuir*, 2002, 18: 2717-2726.
Garg et al, "Self-assembled monolayers based on chelating aromatic dithiols on gold," *Langmuir*, 1998, 14: 3815-3819.
Gerasimov and Lai, "An electrochemical peptide-based biosensing platform for HIV detection," *Chem. Commun.*, 2010, 46:395-397.
Gerasimov and Lai, "Design and characterization of an electrochemical peptide-based sensor fabricated via "click" chemistry," *Chem. Commun.*, 2011, 47:8688-8690.
Ginorta and Kulkarni, "Solution Structure of Physiological Cu(His)2: Novel Considerations into Imidazole Coordination," *Inorg. Chem.*, 2009, 48:7000-7002.
Hochuli et al., "New metal chelate adsorbent selective for proteins and peptides containing neighbouring histidine residues," *J. Chromatog.*, 1987, 411:177-184.
Hong et al., "Electrochemically Protected Copper(I)-Catalyzed Azide-Alkyne Cycloaddition," *ChemBioChem*, 2008, 9:1481-1486.
Hwang et al., "Faradaic impedance titration and control of electron transfer of 1 (12-mercaptododecyl)imidazole monolayer on a gold electrode," *Electrochim. Acta*, 2008, 53:2630-2636.
Immoos et al., "DNA-PEG-DNA Triblock Macromolecules for Reagentless DNA Detection," *J. Am. Chem. Soc.*, 2004, 126:10814.
Jayaram and Beveridge, "Modeling DNA in Aqueous Solutions: Theoretical and Computer Simulation Studies on the Ion Atmosphere of DNA," *Annu. Rev. Biophys. Biomol. Struct.*, 1996, 25:367-394.
Kerman and Kraatz, "Electrochemical probing of HIV enzymes using ferrocene-conjugated peptides on surfaces," *Analyst*, 2009, 134:2400-2404.
Kolb et al., "Click Chemistry: Diverse Chemical Function from a Few Good Reactions," *Angew. Chem.*, 2001, 40:2004-2021.
Ku et al., "Surface Patterning with Fluorescent Molecules Using Click Chemistry Directed by Scanning Electrochemical Microscopy," *J. Am. Chem. Soc.*, 2008, 130:2392-2393.
Lacour et al., "Synthesis, Enantiomeric Conformations, and Stereodynamics of Aromatic ortho-Substituted Disulfones," *Org. Lett.*, 2001, 3:1407-1410.
Lai et al., "Aptamer-Based Electrochemical Detection of Picomolar Platelet-Derived Growth Factor Directly in Blood Serum," *Anal. Chem.*, 2007, 79:229-233.
Lai et al., "Differential Labeling of Closely Spaced Biosensor Electrodes via Electrochemical Lithography," *Langmuir*, 2006, 22:1932-1936.
Lai et al., "Rapid, sequence-specific detection of unpurified PCR amplicons via a reusable, electrochemical sensor," *Proc. Natl. Acad. Sci.*, 2006, 103:4017-4021.
Lim et al., "Direct and nondestructive verification of PNA immobilization using click chemistry," *Biochem. Biophys. Res. Comm.*, 2008, 376:633-636.
Liu et al., "Molecular simulations to determine the chelating mechanisms of various metal ions to the His-tag motif: a preliminary study," *J Biomol. Struct. Dyn.*, 2003, 21:31-41.
Love et al., "Self-Assembled Monolayers of Thiolates on Metals as a Form of Nanotechnology," *Chem. Rev.*, 2005, 105:1103-1169.
Lubin et al., "Sequence-Specific, Electronic Detection of Oligonucleotides in Blood, Soil, and Foodstuffs with the Reagentless, Reusable E-DNA Sensor," *Anal. Chem.*, 2006, 78:5671-5677.
Lubin et al., "Effects of Probe Length, Probe Geometry, and Redox-Tag Placement on the Performance of the Electrochemical E-DNA Sensor," *Anal. Chem.*, 2009, 81:2150-2158.
Maly et al., "Monolayers of Natural and Recombinant Photosystem II on Gold Electrode—Potentials for Use as Biosensors for Detection of Herbicides," *Anal. Lett.*, 2004, 37(8):1645-1656.
Mirmomtaz et al., "Quantitative Study of the Effect of Coverage on the Hybridization Efficiency of Surface-Bound DNA Nanostructures," *Nano Lett.*, 2008, 8:4134-4139.
Mora et al., "Adsorption of Divalent Cations on DNA," *Biophysical J.*, 2004, 87:2897-2904.
Moses and Moorhouse, "The growing applications of click chemistry," *Chem. Soc. Rev.*, 2007, 36:1249-1262.

(56) References Cited

OTHER PUBLICATIONS

O'Connor et al., "A Nernstian electron source model for the ac voltammetric response of a reversible surface redox reaction using large-amplitude ac voltages," *J. Electroanal. Chem.*, 1999, 466:197-202.

Odenthal and Gooding, "An introduction to electrochemical DNA biosensors," *Analyst*, 2007, 132:603-610.

Ovchenkova et al., "The electronic structure of metal/alkane thiol self-assembled monolayers/metal junctions for magnetoelectronics applications," *Chem Physics Lett.*, 2003, 381:7-13.

Ricci et al., "Linear, redox modified DNA probes as electrochemical DNA sensors," *Chem. Commun.*, 2007, 36:3768.

Ricci et al., "Effect of Molecular Crowding on the Response of an Electrochemical DNA Sensor," *Langmuir*, 2007, 23:6827-6834.

Rozkiewicz et al., "'Click' Chemistry by Microcontact Printing," *Angew. Chem.*, 2006, 45:5292-5296.

Sassolas et al., "DNA Biosensors and Microarrays," *Chem. Rev.*, 2008, 108:109-139.

Shervedani and Mozaffari, "Copper(II) Nanosensor Based on a Gold Cysteamine Self-Assembled Monolayer Functionalized with Salicylaldehyde," *Anal. Chem.*, 2006, 78:4957-4963.

Subramanian et al., "Mono and dithiol surfaces on surface plasmon resonance biosensors for detection *Staphylococcus aureus*," *Sensors and Actuators B*, 2006, 114: 192-198.

Sumner and Creager, "Topological Effects in Bridge-Mediated Electron Transfer Between Redox Molecules and Metal Electrodes," *J Am. Chem. Soc.*, 2000, 122:11914-11920.

Sumner et al., "Long-Range Heterogeneous Electron Transfer Between Ferrocene and Gold Mediated by n-Alkane and N-Alkyl-Carboxamide Bridges," *J Phys. Chem. B*, 2000, 104:7449-7454.

Sundberg and Martin, "Interactions of histidine and other imidazole derivatives with transition metal ions in chemical and biological systems," *Chem. Soc. Rev.*, 1974, 74:471-517.

Suzuki et al., "36nm-Si Pillar Fabricated by the Three Dimensional (3D) Thermal Oxidation of Silicon," 204th Electrochem. Soc. Meeting, 2004, 341-343.

Suzuki et al., "Study of Oxide Charge by X-ray Photoelectron Spectroscopic and C-V Measurements," *204th Electrochem. Soc. Meeting*, 2004, 346-349.

Valenti et al., "The binding of Ni(II) ions to hexahistidine as a model system of the interaction between nickel and His-tagged proteins," *J. Inorg. Biochem.*, 2006, 100:192-200.

Wei et al., "Direct Wiring of Cytochrome c's Heme Unit to an Electrode: Electrochemical Studies," *J. Am. Chem. Soc.*, 2002, 124:9591-9599.

Xiao et al., "Label-Free Electronic Detection of Thrombin in Blood Serum by Using an Aptamer-Based Sensor," *Angew. Chem.*, 2005, 117:5592-5595.

Xiao et al., "Single-step electronic detection of femtomolar DNA by target-induced strand displacement in an electrode-bound duplex," *Proc. Natl. Acad. Sci.*, 2006, 103:16677-16680.

Yang et al., "Folding-based electrochemical DNA sensor fabricated on a gold-plated screen-printed carbon electrode," *Chem. Comm*, 2009, 20:2902-2904.

\* cited by examiner

SELF-ASSEMBLED MONOLAYERS AND METHODS FOR USING THE SAME IN BIOSENSING APPLICATIONS

CROSS-REFERENCE TO RELATED APPLICATIONS

This application is a continuation of U.S. application Ser. No. 13/491,168, filed Jun. 7, 2015, which claims the benefit of U.S. Application Ser. No. 61/622,727, filed Apr. 11, 2012 and U.S. Provisional Application Ser. No. 61/494,026, filed Jun. 7, 2011. The disclosures of the prior applications are considered part of (and are incorporated by reference in) the disclosure of this application.

GRANT SUPPORT

This work was supported in part by the National Science Foundation (NSF Grant EPSCoR RII (2010-2015)). The Government may have certain rights in the invention, as specified by law.

FIELD OF THE INVENTION

The present invention relates to new self-assembled monolayers (SAMs) that are useful in the fabrication of biosensors.

BACKGROUND OF THE INVENTION

The present invention relates to biosensors that are capable of rapidly quantifying the concentration of biomolecules in a sample solution with high accuracy in a simplified manner, and to methods of producing same.

The detection of a ligand by a receptor (for example, detection of a hormone, an antigen or a pathogenic agent) is important in the diagnosis of diseases and finding of useful biomolecules. Many rapid test methods for detecting ligands with high selectivity and sensitivity have been developed. These include radio-activity-based assays, chemiluminescence assays, magnetic based assays, and fluorescence or colorimetric assays. Immunoassays, such as enzyme-linked immunosorbent assay (ELISA), enzyme immunoassay (EIA), and radioimmunoassay (RIA), are also well known for the detection of ligands such as hormones, antigens or antibodies. The basic principle in many of these assays is that a marker-conjugated (for example, an enzyme-, chromogen-, fluorogen-, or radionucleotide-conjugated) antibody permits antigen detection upon antibody binding. In order for this interaction to be detected as a change in color, fluorescent or radioactive complexes, significant numbers of antibodies must be bound to a correspondingly large number of antigen epitopes. The resulting labeled binding complex often must be isolated from the labeled marker molecules for detection.

Although the prior art methods for measuring biological analytes of interest are useful, many problems arise in the application of these methods in biosensor platforms, such as low sensitivity, selectivity and stability of the sensing device. Moreover, existing methods are often time intensive, tedious and costly. Accordingly, there remains a need for sensitive and robust screening methods for detecting biomolecules in a sample.

Electrochemical biosensors such as an electrochemical peptide-based (E-PB) sensor offer a convenient way to conjugate biosensing elements labelled with a redox molecule on a gold-electrode surface. To date, the most straightforward method to fabricate an E-PB sensor involves direct adsorption of thiolated peptide probes onto the gold electrode surface. Despite being a valuable probe immobilization strategy, conventional methods lacks general surface modification versatility.

SUMMARY OF THE INVENTION

Applicants have found that, surprisingly, a more convenient approach is to first assemble a self-assembled monolayer (SAM) containing terminal reactive groups that may serve as a platform onto which one can couple different binding partners to the monolayer. The SAM-peptide immobilization approach described herein offers a significant advantage of versatility in sensor fabrication.

The present invention provides compounds that form self-assembled monolayers that are useful in the fabrication of biosensors. In particular, the present invention provides self-assembled monolayers comprising compounds of Formula I or II:

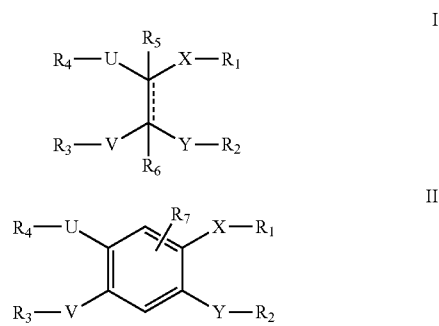

wherein constituent members are provided herein below.

The present invention further provides a method for detecting one or more biomolecules in a sample which comprises the steps of (a) providing a component that comprises a self-assembled monolayer comprising a compound of Formula I or II; (b) binding a multivalent cation to the monolayer; (c) capturing a binding partner onto the monolayer, wherein the binding partner comprises a detectable marker and a moiety capable of binding the multivalent cation; (d) exposing the sample to the monolayer component; and (e) detecting a signal of the detectable marker.

The present invention further provides methods for detecting any ligand for a binding partner, such as, without limitation, small-molecules, hormones, proteins, peptides, nucleic acids, lipids, antigens or antibodies.

The present invention further provides methods for detecting specific ligands such as anti-peanut antigen and anti-HIV-p24 antibody.

The present invention further provides a kit for detecting one or more target molecules in a sample.

DETAILED DESCRIPTION

Figure 1:
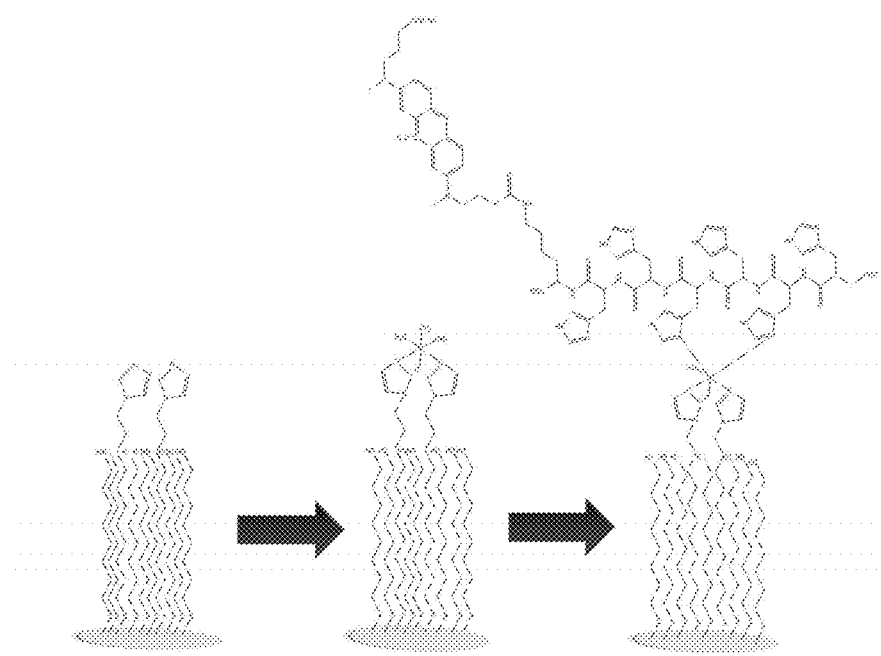
FIG. 1 is a schematic showing immobilization of a histidine-tagged methylene blue ($His_6$-MB) construct onto an imidazole-nickel-bound self-assembled monolayer (SAM) of the invention.

The instant invention provides, inter alia, self-assembled monolayers (SAMs) that can be used to immobilize binding partners such as peptides in the fabrication of electrochemical peptide-based sensors.

Compounds

In some embodiments, the present invention provides a self-assembled monolayer comprising a compound of Formula I or II:

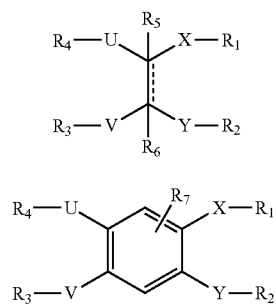

wherein:
a dashed line indicates an optional bond;
$R_1$-$R_4$ are each, independently, $C_{1-20}$alkyl, $SR_a$, OH, $COR_b$, heterocyclyl, heteroaryl, alkenyl, alkynyl, CN, $N_3$, or halo;
$R_5$ and $R_6$ are each, independently, absent, H, or $R_c$;
$R_7$ is 0-2 $R_c$ groups.
X, Y, U, and V are each, independently, $C_{1-20}$alkyl, $C_{2-20}$alkenyl, $C_{2-20}$alkynyl, $C_{1-20}$alkyl ether, $C_{2-20}$alkenyl ether, or $C_{2-20}$alkynyl ether;
$R_a$ is H, $C_{1-20}$alkyl, C(O)H, CO—($C_{1-20}$alkyl), SH, or S($C_{1-20}$alkyl);
$R_b$ is $C_{0-20}$hydroxyl, $C_{3-10}$heterocycloalkyl, $C_{5-10}$aryl, $C_{5-10}$heteroaryl, or $NR^IR^{II}$;
$R_c$ is alkyl, alkenyl, alkynyl, cycloalkyl, aryl, heteroaryl, hydroxyl, halo, haloalkyl, haloalkoxy, cyano, nitro, azido, amino, alkylamino, dialkylamino, carboxy, carboxyalkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl, or arylsufonyl; and $R^I$ and $R^{II}$ are each, independently selected from H, substituted or unsubstituted alkyl,
or $R^I$ and $R^{II}$ come together to form a 4-10-membered substituted or unsubstituted heterocyclic ring.

In some embodiments, at least one of $R_1$-$R_4$ is $SR_a$.

In some embodiments, at least one of $R_1$-$R_4$ is S($C_{1-20}$alkyl), SC(O)($C_{1-20}$alkyl), SH, or S($C_{1-20}$alkyl).

In some embodiments, at least one of $R_1$-$R_4$ is SH or SC(O)($C_{1-20}$alkyl).

In some embodiments, at least one of $R_1$-$R_4$ is SH.

In some embodiments, at least one of $R_1$-$R_4$ is SC(O)($C_{1-20}$ alkyl).

In some embodiments, at least one of $R_1$-$R_4$ is SC(O)CH$_3$.

In some embodiments, $R_1$ and $R_2$ are $SR_a$.

In some embodiments, $R_1$ and $R_2$ are S($C_{1-20}$alkyl), SC(O)($C_{1-20}$alkyl), SH, or S($C_{1-20}$alkyl).

In some embodiments, $R_1$ and $R_2$ are SH or SC(O)($C_{1-20}$ alkyl).

In some embodiments $R_1$ and $R_2$ are SH.

In some embodiments, $R_1$ and $R_2$ are SC(O)($C_{1-20}$alkyl).

In some embodiments, $R_1$ and $R_2$ are SC(O)CH$_3$.

In some embodiments, at least one of $R_1$-$R_4$ is OH, C(O)$R_b$, $N_3$, heterocyclyl, or heteroaryl.

In some embodiments, at least one of $R_1$-$R_4$ is OH.

In some embodiments, at least one of $R_1$-$R_4$ is heterocyclyl or heteroaryl.

In some embodiments, at least one of $R_1$-$R_4$ is heterocyclyl.

In some embodiments, at least one of $R_1$-$R_4$ is 1,4,7-triazacyclononanyl.

In some embodiments, at least one of $R_1$-$R_4$ is heteroaryl.

In some embodiments, at least one of $R_1$-$R_4$ is pyridyl or imidazolyl.

In some embodiments, at least one of $R_1$-$R_4$ is pyridyl.

In some embodiments, at least one of $R_1$-$R_4$ is imidazolyl.

In some embodiments, at least one of $R_1$-$R_4$ is azido.

In some embodiments, at least one of $R_1$-$R_4$ is CN.

In some embodiments, $R_3$ and $R_4$ OH, C(O)$R_b$, $N_3$, heterocyclyl, or heteroaryl.

In some embodiments, $R_3$ and $R_4$ are OH.

In some embodiments, $R_3$ and $R_4$ are heterocyclyl or heteroaryl.

In some embodiments, $R_3$ and $R_4$ are heterocyclyl.

In some embodiments, $R_3$ and $R_4$ are 1,4,7-triazacyclononanyl.

In some embodiments, $R_3$ and $R_4$ are heteroaryl.

In some embodiments, $R_3$ and $R_4$ are pyridyl or imidazolyl.

In some embodiments, $R_3$ and $R_4$ are pyridyl.

In some embodiments, $R_3$ and $R_4$ are imidazolyl.

In some embodiments, $R_3$ and $R_4$ are azido.

In some embodiments, $R_3$ and $R_4$ are CN.

In some embodiments, at least one of X, Y, U, and V is $C_{1-20}$alkyl.

In some embodiments, at least one of X, Y, U, and V is $C_{1-8}$alkyl.

In some embodiments, at least one of X, Y, U, and V is $C_{1-6}$alkyl.

In some embodiments, X, Y, U, and V are $C_{1-20}$alkyl.

In some embodiments, X, Y, U, and V are $C_{1-8}$alkyl.

In some embodiments, X, Y, U, and V are $C_{1-6}$alkyl.

In some embodiments, at least one of X, Y, U, and V is $C_{2-20}$alkynyl.

In some embodiments, at least one of X, Y, U, and V is $C_2$alkynyl.

In some embodiments, X, Y, U, and V are $C_{2-20}$alkynyl.

In some embodiments, X, Y, U, and V are $C_2$alkynyl.

In some embodiments, $R_5$ and $R_6$ are absent.

In some embodiments, $R_7$ is 0 $R_c$ groups.

In some embodiments, the compound is a compound of Formula I.

In some embodiments, the compound is a compound of Formula II.

In some embodiments, the compound is a compound of Formula I, wherein:
 $R_1$ and $R_2$ are $SR_a$;
 $R_3$ and $R_4$ are OH;
 X, Y, U, and V are each, independently, $C_{1-20}$alkyl; and
 $R_5$ and $R_6$ are absent.

In some embodiments, the compound is a compound of Formula I, wherein:
 $R_1$ and $R_2$ are SH or SCO—($C_{1-20}$alkyl);
 $R_3$ and $R_4$ are OH;
 X, Y, U, and V are each, independently, $C_{2-8}$alkyl; and
 $R_5$ and $R_6$ are absent.

In some embodiments, the compound is a compound of Formula I, wherein:
 $R_1$ and $R_2$ are SH or $SCOCH_3$;
 $R_3$ and $R_4$ are OH;
 X and Y are $C_8$alkyl;
 U, and V are $C_2$alkyl; and
 $R_5$ and $R_6$ are absent.

In some embodiments, the compound is a compound of Formula I, wherein:
 $R_1$ and $R_2$ are $SR_a$;
 $R_3$ and $R_4$ are OH;
 X, Y, U, and V are each, independently, $C_{1-20}$alkyl; and
 $R_5$ and $R_6$ are H.

In some embodiments, the compound is a compound of Formula I, wherein:
 $R_1$ and $R_2$ are SH or SCO—($C_{1-20}$alkyl);
 $R_3$ and $R_4$ are OH;
 X, Y, U, and V are each, independently, $C_{2-8}$alkyl; and
 $R_5$ and $R_6$ are H.

In some embodiments, the compound is a compound of Formula I, wherein:
 $R_1$ and $R_2$ are SH or $SCOCH_3$;
 $R_3$ and $R_4$ are OH;
 X and Y are $C_8$alkyl
 U, and V are $C_2$alkyl; and
 $R_5$ and $R_6$ are H.

In some embodiments, the compound is a compound of Formula I, wherein:
 $R_1$ and $R_2$ are $SR_a$;
 $R_3$ and $R_4$ are heteroaryl;
 X, Y, U, and V are each, independently, $C_{1-20}$alkyl; and
 $R_5$ and $R_6$ are absent.

In some embodiments, the compound is a compound of Formula I, wherein:
 $R_1$ and $R_2$ are SH or SCO—($C_{1-20}$alkyl);
 $R_3$ and $R_4$ are heteroaryl;
 X, Y, U, and V are each, independently, $C_{2-8}$alkyl; and
 $R_5$ and $R_6$ are absent.

In some embodiments, the compound is a compound of Formula I, wherein:
 $R_1$ and $R_2$ are SH or $SCOCH_3$;
 $R_3$ and $R_4$ are heteroaryl;
 X and Y are $C_8$alkyl
 U, and V are $C_2$alkyl; and
 $R_5$ and $R_6$ are absent.

In some embodiments, the compound is a compound of Formula I, wherein:
 $R_1$ and $R_2$ are SH or $SCOCH_3$;
 $R_3$ and $R_4$ are imidazolyl;
 X and Y are $C_8$alkyl
 U, and V are $C_2$alkyl; and
 $R_5$ and $R_6$ are absent.

In some embodiments, the compound is a compound of Formula II, wherein:
 $R_1$ and $R_2$ are $SR_a$;
 $R_3$ and $R_4$ are heteroaryl;
 X, Y, U, and V are each, independently, $C_{1-20}$alkyl; and
 $R_7$ is absent.

In some embodiments, the compound is a compound of Formula II, wherein:
 $R_1$ and $R_2$ are SH or SCO—($C_{1-20}$alkyl);
 $R_3$ and $R_4$ are heteroaryl;
 X, Y, U, and V are each, independently, $C_{1-20}$alkyl; and
 $R_7$ is absent.

In some embodiments, the compound is a compound of Formula II, wherein:
 $R_1$ and $R_2$ are SH or SCO—$C_3$alkyl;
 $R_3$ and $R_4$ are imidazolyl;
 X, Y, U, and V are each, independently, $C_{1-8}$alkyl; and
 $R_7$ is absent.

In some embodiments, the compound is a compound of Formula II, wherein:
 $R_1$ and $R_2$ are SH or SCO—$C_3$alkyl;
 $R_3$ and $R_4$ are imidazolyl;
 X and Y are each $C_8$alkyl;
 U and V are each $C_2$alkyl; and
 $R_7$ is absent.

In some embodiments, the compound is a compound of Formula II, wherein:
 $R_1$ and $R_2$ are SH or SCO—($C_{1-20}$alkyl);
 $R_3$ and $R_4$ are $C_{1-20}$alkyl;
 X, Y, U, and V are each, independently, $C_{1-20}$alkyl; and
 $R_7$ is absent.

In some embodiments, the compound is a compound of Formula II, wherein:
 $R_1$ and $R_2$ are SH or SCO—$C_3$alkyl;
 $R_3$ and $R_4$ are $C_1$alkyl;
 X, Y, U, and V are each $C_6$ alkyl; and
 $R_7$ is absent.

In some embodiments, the compound is a compound of Formula II, wherein:
 $R_1$ and $R_2$ are SH or SCO—$C_3$alkyl;
 $R_3$ and $R_4$ are pyridyl;
 X and Y are each $C_6$alkynyl;
 U and V are each $C_2$alkynyl; and
 $R_7$ is absent.

In some embodiments, the compound is a compound of Formula II, wherein:
 $R_1$ and $R_2$ are SH or SCO—($C_{1-20}$alkyl);
 $R_3$ and $R_4$ are OH;
 X, Y, U, and V are $C_4$alkyl; and
 $R_7$ is absent.

In some embodiments, the compound is a compound of Formula II, wherein:
 $R_1$ and $R_2$ are SH or SCO—($C_{1-20}$alkyl);
 $R_3$ and $R_4$ are OH or $N_3$;
 X, Y, U, and V are $C_{2-6}$alkyl; and
 $R_7$ is absent.

In some embodiments, the compound is a compound of Formula II, wherein:
$R_1$ and $R_2$ are SH or SCO—($C_{1-20}$alkyl);
$R_3$ and $R_4$ are $N_3$;
X, Y, U, and V are $C_{2-6}$alkyl; and
$R_7$ is absent.

In some embodiments, the compound is a compound of Formula II, wherein:
$R_1$ and $R_2$ are SH or SCO—($C_{1-20}$alkyl);
$R_3$ and $R_4$ are $N_3$;
X, Y, U, and V are $C_3$alkyl; and
$R_7$ is absent.

In some embodiments, the compound is a compound of Formula II, wherein:
$R_1$ and $R_2$ are SH or SCO—($C_{1-20}$alkyl);
$R_3$ and $R_4$ are OH or $N_3$;
X, Y, U, and V are $C_5$alkyl; and
$R_7$ is absent.

In some embodiments, wherein the compound is a compound of Formula II, wherein:
$R_1$ and $R_2$ are SH or SCO—($C_{1-20}$alkyl);
$R_3$ and $R_4$ are imidazolyl;
X, Y, U, and V are $C_4$alkyl; and
$R_7$ is absent.

In some embodiments, the compound is a compound of Formula II, wherein:
$R_1$ and $R_2$ are SH or SCO—($C_{1-20}$alkyl);
$R_3$ and $R_4$ are imidazolyl;
X, Y, U, and V are $C_4$alkyl; and
$R_7$ is absent.

In some embodiments, the compound is a compound of Formula II, wherein:
$R_1$ and $R_2$ are SH or SCO—$C_3$alkyl;
$R_3$ and $R_4$ are imidazolyl;
X and Y are each $C_2$alkyl;
U and V are each $C_6$alkyl; and
$R_7$ is absent.

In some embodiments, at least one of $R_3$ or $R_4$ is $C(O)R_b$.
In some embodiments, $R_b$ is $NR^IR^{II}$.
In some embodiments, $NR^IR^{II}$ is a triazacyclononane group.
In some embodiments, the triazacyclononane group is substituted with an alkylcarboxylate.
In some embodiments, $NR^I R^{II}$ is $NH(C_{1-20}$alkyl).
In some embodiments, the $NH(C_{1-20}$alkyl) is substituted with a nitrilotriacetic acid.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$alkyl, $C_4$alkyl, $C_5$alkyl, and $C_6$ alkyl.

For compounds of the invention in which a variable appears more than once, each variable can be a different moiety selected from the Markush group defining the variable. For example, where a structure is described having two $R^1$ groups that are simultaneously present on the same compound; the two R groups can represent different moieties selected from the Markush group defined for R. It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can, for example, contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCI_3$, $CHCl_2$, $C_2Cl_5$, and the like. An alkyl group in which all of the hydrogen atoms are replaced with halogen atoms can be referred to as "perhaloalkyl."

As used herein, "alkylene" or "alkylenyl" refers to a bivalent alkyl group. An example alkylene group is methylene or ethylene.

As used herein, "alkenylene" or "alkenylenyl" refers to a bivalent alkenyl group. As used herein, "carbocyclyl" groups are saturated (i.e., containing no double or triple bonds) or unsaturated (i.e., containing one or more double or triple bonds) cyclic hydrocarbon moieties. Carbocyclyl groups can be mono- or polycyclic (e.g., having 2, 3 or 4 fused rings) or spirocyclic. Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcamyl, adamantyl, phenyl, and the like. Carbocyclyl groups can be aromatic (e.g., "aryl") or non-aromatic (e.g., "cycloalkyl"). In some embodiments, carbocyclyl groups can have from about 3 to about 30 carbon atoms, about 3 to about 20, about 3 to about 10, or about 3 to about 7 carbon atoms.

As used herein, the term "alkyl ether" refers to an alkyl group or a cycloalkyl group as defined herein, having at least one oxygen incorporated into the alkyl chain e.g., methyl ethyl ether, diethyl ether, tetrahydrofuran. In some embodiments alkyl ether groups can have from 1-20 carbon atoms. In some embodiments, the alkyl ether is a $C_{1-20}$polyether group.

As used herein, the term "alkenyl ether" refers to an alkenyl group or a cycloalkenyl group as defined herein, having at least one oxygen incorporated into the alkene chain. In some embodiments alkenyl ether groups can have from 1-20 carbon atoms.

As used herein, the term "alkynyl ether" refers to an alkynyl group or a cycloalkynyl group as defined herein, having at least one oxygen incorporated into the alkyne chain. In some embodiments alkynyl ether groups can have from 1-20 carbon atoms.

As used herein, "aryl" refers to an aromatic carbocyclyl group including monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocyclyl groups including cyclized alkyl, alkenyl, and alkynyl groups. Cycloalkyl groups can include bi- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like.

As used herein, "heterocyclyl" or "heterocycle" refers to a saturated or unsaturated carbocyclyl group wherein one or more of the ring-forming carbon atoms of the carbocyclyl group is replaced by a heteroatom such as O, S, or N. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can be characterized as having 3-14 ring-forming atoms. In some embodiments, heterocyclyl groups can contain, in addition to at least one heteroatom, from about 1 to about 20, about 2 to about 10, or about 2 to about 7 carbon atoms and can be attached through a carbon atom or heteroatom. In further embodiments, the heteroatom can be oxidized (e.g., have an oxo or sulfindo substituent) or a nitrogen atom can be quatemized Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, deca-hydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperindin-1-yl, piperazin-1-yl, pyrrolidin-1-yl, isoquinol-2-yl, pyridin-1-yl, 3,6-dihydro-pyridin-1-yl, 2,3-dihydroindol-1-yl, 1,3,4,9-tetrahydrocarbolin-2-yl, thieno[2,3-c]pyridin-6-yl, 3,4, 10, 10a-tetrahydro-1H-pyrazino[1,2-a]indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b-hexahydro-2H-benzo[f]isoquinolin-3-yl, 3,3a,8,8a-tetrahydro-1H-2-aza-cyclopenta[a]inden-2-yl, and 2,3,4,7-tetrahydro-1H-azepin-1-yl, azepan-1-yl. Also included are fused ring and spiro compounds containing, for example, the above heterocycles.

As used herein, "heteroaryl" groups are aromatic heterocyclyl groups and include monocyclic and polycyclic (e.g., having 2, 3 or 4 fused rings) aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocyclyl groups including cyclized alkyl, alkenyl, and alkynyl groups where one or more of the ring-forming carbon atoms is replaced by a heteroatom such as an O, N, or S atom. Example heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo. As used herein, "alkoxy" refers to an —O-alkyl group. Example alkoxy groups include methoxy, ethoxy, propoxy (e.g., n-propoxy and isopropoxy), t-butoxy, and the like. As used herein, "aryloxy" refers to an —O-aryl group. An example aryloxy group is phenoxy. As used here, "haloalkoxy" refers to an —O-haloalkyl group. An example haloalkoxy group is OCF3. As used herein, "carbocyclylalkyl" refers to an alkyl moiety substituted by a carbocyclyl group. Example carbocyclylalkyl groups include "aralkyl" (alkyl substituted by aryl ("arylalkyl")) and "cycloalkylalkyl" (alkyl substituted by cycloalkyl). In some embodiments, carbocyclylalkyl groups have from 4 to 24 carbon atoms.

As used herein, "heterocyclylalkyl" refers to an alkyl moiety substituted by a heterocarbocyclyl group. Example heterocarbocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one ring-forming heteroatom.

As used herein, "amino" refers to an $NH_2$ group. "Alkylamino" refers to an amino group substituted by an alkyl group and "dialkylamino" refers to an amino group substituted by two alkyl groups.

As used herein, "aminocarbonyl" refers to $CONH_2$.

As used herein, "alkylaminocarbonyl" refers to CONH (alkyl).

As used herein, "alkylaminocarbonyl" refers to CON $(alkyl)_2$.

As used herein, "carboxy" or "carboxyl" refers to COOH.

As used herein, "carboxy alkyl ester" refers to COO-alkyl.

As used herein, "carboxy aryl ester" refers to COO-aryl.

As used herein, "hydroxy" refers to OH.

As used herein, "mercapto" refers to SH.

As used herein, "sulfinyl" refers to SO.

As used herein, "sulfonyl" refers to $SO_2$.

As used herein, "aminosulfonyl" refers to $SO_2NH_2$.

As used herein, "alkylaminosulfonyl" refers to $SO_2NH$ (alkyl).

As used herein, "dialkylaminosulfonyl" refers to $SO_2N$ $(alkyl)_2$.

As used herein, "arylsulfonyl" refers to SO-aryl.

As used herein, "arylsulfmyl" refers to SO-aryl.

As used herein, "alkylsulfonyl" refers to $SO_2$-alkyl.

As used herein, "alkylsulfinyl" refers to SO-alkyl.

Unless otherwise indicated, the compounds provided in the above formula are meant to include salts, enantiomers, diastereomers, racemic mixtures, crystalline forms, non-crystalline forms, amorphous forms, hydrates and solvates thereof.

When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention may contain both basic and acidic functionalities that allow the compounds to be converted into either base or acid addition salts. The neutral forms of the compounds of the present invention may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As noted above, some of the compounds of the present invention possess chiral or asymmetric carbon atoms (optical centers) or double bonds; the racemates, diastereomers, geometric isomers and individual optical isomers are all intended to be encompassed within the scope of the present invention.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as keto-enol tautomers. Tautomeric forms can be in equilibrium or sterically locked into one form by appropriate substitution.

Some of the compounds of the invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In some embodiments, the compounds of Formula I are selected from:
- (Z)-3,4-bis(8-mercaptooctyl)hex-3-ene-1,6-diol;
- (Z)-(9,10-bis(2-hydroxyethyl)octadec-9-ene-1,18-diyl)diethanethioate;
- (3R,4S)-3,4-bis(8-mercaptooctyl)hexane-1,6-diol;
- ((9R,10S)-9,10-bis(2-hydroxyethyl)octadecane-1,18-diyl) diethanethioate;
- (3R,4R)-3,4-bis(8-mercaptooctyl)hexane-1,6-diol;
- ((9R,10R)-9,10-bis(2-hydroxyethyl)octadecane-1,18-diyl) diethanethioate;
- (Z)-9,10-bis(2-(1H-imidazol-1-yl)ethyl)octadec-9-ene-1, 18-dithiol; and
- (Z) 9,10-bis(2-(1H-imidazol-1-yl)ethyl)octadec-9-ene-1,18-diyl)diethanethioate.

In some embodiments, the compounds of Formula II are selected from:
- 2,2'-(4,5-bis(6-mercaptohexyl)-1,2-phenylene)diethanol;
- ((4,5-bis(2-hydroxyethyl)-1,2-phenylene)bis(hexane-6,1-diyl))diethanethioate;
- 5,5'-(4,5-bis(6-mercaptohexyl)-1,2-phenylene)bis(pentan-1-ol);
- ((4,5-bis(5-hydroxypentyl)-1,2-phenylene)bis(hexane-6,1-diyl))diethanethioate;
- 8,8'-(4,5-bis(2-(1H-imidazol-1-yl)ethyl)-1,2-phenylene)bis (octane-1-thiol);
- ((4,5-bis(2-(1H-imidazol-1-yl)ethyl)-1,2-phenylene)bis(octane-8,1-diyl))diethanethioate;
- 6,6'-(4,5-diheptyl-1,2-phenylene)bis(hexan-1-ol);
- 6,6'-(4,5-bis(pyridin-2-ylethynyl)-1,2-phenylene)bis(hex-5-yne-1-thiol);
- ((4,5-bis(pyridin-2-ylethynyl)-1,2-phenylene)bis(hex-5-yne-6,1-diyl))diethanethioate;
- 4,4'-(4,5-bis(4-mercaptobutyl)-1,2-phenylene)bis(butan-1-ol);
- ((4,5-bis(4-hydroxybutyl)-1,2-phenylene)bis(butane-4,1-diyl))diethanethioate;
- 2-(2-(2-azidoethyl)-4,5-bis(6-mercaptohexyl)phenyl)ethanol;
- ((4-(2-azidoethyl)-5-(2-hydroxyethyl)-1,2-phenylene)bis (hexane-6,1-diyl))diethanethioate;
- 6,6'-(4,5-bis(2-azidoethyl)-1,2-phenylene)bis(hexane-1-thiol);
- ((4,5-bis(2-azidoethyl)-1,2-phenylene)bis(hexane-6,1-diyl)) diethanethioate;

5,5'-(4,5-bis(5-azidopentyl)-1,2-phenylene)bis(pentane-1-thiol);
((4,5-bis(5-azidopentyl)-1,2-phenylene)bis(pentane-5,1-diyl))diethanethioate;
5-(2-(5-azidopentyl)-4,5-bis(5-mercaptopentyl)phenyl)pentan-1-ol;
((4-(5-azidopentyl)-5-(5-hydroxypentyl)-1,2-phenylene)bis(pentane-5,1-diyl))diethanethioate;
4,4'-(4,5-bis(4-(1H-imidazol-1-yl)butyl)-1,2-phenylene)bis(butane-1-thiol);
((4,5-bis(4-(1H-imidazol-1-yl)butyl)-1,2-phenylene)bis(butane-4,1-diyl))diethanethioate;
2,2'-(4,5-bis(6-(1H-imidazol-1-yl)hexyl)-1,2-phenylene)diethanethiol;
((4,5-bis(6-(1H-imidazol-1-yl)hexyl)-1,2-phenylene)bis(ethane-2,1-diyl))diethanethioate;
5,5'-(4,5-bis(5-mercaptopentyl)-1,2-phenylene)bis(pentan-1-ol);
((4,5-bis(5-hydroxypentyl)-1,2-phenylene)bis(pentane-5,1-diyl))diethanethioate;
6,6'-(4,5-bis(2-(1H-imidazol-1-yl)ethyl)-1,2-phenylene)bis(hexane-1-thiol); and
((4,5-bis(2-(1H-imidazol-1-yl)ethyl)-1,2-phenylene)bis(hexane-6,1-diyl))diethanethioate.

In some embodiments of the invention, the compounds of the invention comprise:
1-(11-mercaptoundecyl)imidazole
(Z)-9,10-bis(2-(1H-imidazol-1-yl)ethyl)octadec-9-ene-1,18-dithiol;
(Z)(9,10-bis(2-(1H-imidazol-1-yl)ethyl)octadec-9-ene-1,18-diyl)diethanethioate
6,6'-(4,5-bis(2-(1H-imidazol-1-yl)ethyl)-1,2-phenylene)bis(hexane-1-thiol); and
((4,5-bis(2-(1H-imidazol-1-yl)ethyl)-1,2-phenylene)bis(hexane-6,1-diyl)).

As noted above, some of the compounds of the present invention possess chiral or asymmetric carbon atoms (optical centers) or double bonds; the racemates, diastereomers, geometric isomers and individual optical isomers are all intended to be encompassed within the scope of the present invention.

The compounds of Formula I and II have unique structural features that are useful for several applications. In particular, the inventive compounds contain two amphiphile chains that are joined by a non-polar linker comprising a carbon-carbon single, double or arene bond. This allows for highly organized and uniform binding of the amphiphile chains to a surface for the formation of self-assembled monolayers. The compounds of Formula I and II are believed to provide enhanced stability in monolayer structures compared to single-chain amphiphiles due to cooperative multivalent bonding of two amphiphile chains. The inventive compounds are also believed to adsorb onto metal surfaces at an enhanced rate with high packing density fostered by the cross-linking present in the structures. Upon packing into a monolayer or similar aggregate, the two chains of the cross-linked amphiphile are in close proximity. Varying the functionality on each chain allows construction of functionalized surfaces with an exceptional degree of lateral control.

It has been discovered by Applicants that the structural and functional properties of the monolayer can be modulated by adjusting the linker groups and amphiphile chains of selected amphiphile compounds. For example, the rigidity of the monolayers can be controlled by changing the linker moiety (carbon-carbon single, double or arene bond-linker) and by adjusting the relative position of the crosslinker along the amphiphile chain. A vast array of functional groups may be appended at any point along the amphiphile chain to achieve absolute and independent control over the functionality on each segment. The cross-linking of the two amphiphile chains can be conducted at any location along the amphiphile to fine-tune the flexibility or rigidity at either end of the molecule.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Opimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Green, et al., Protective Groups in Organic Synthesis, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The novel compounds of this invention may be prepared using the reaction pathways and techniques as described below.

A series of compounds of formula 12 are prepared by the methods outlined in scheme 1 (where n of formulas 5-12 and m of formulas 7-12 correspond to appropriate values that would afford compounds of the invention). 1,2-dimethoxybenzene is treated with $H_5IO_6$ and $I_2$ in methanol to afford compound 2, which is reacted $BBr_3$ to provide 3. The diol is then treated with $Tf_2O$ in pyridine to provide the corresponding triflate, which is alkylated with 5 to form product 6. Alkylation of 6 is accomplished by treating with compound 7 to provide product 8. The alkyne and benzyl groups of 8 are removed by hydrogenation to provide compound 9.

The resulting diol is treated with MsCl to form 10, which is then thiylated upon treatment with potassium thioacetate to afford product 11. The acetyl groups are removed with DIBAL-H to produce the final compound 12.

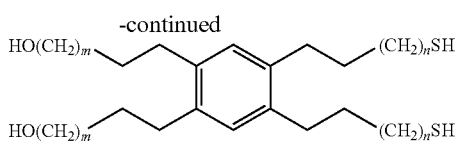

12

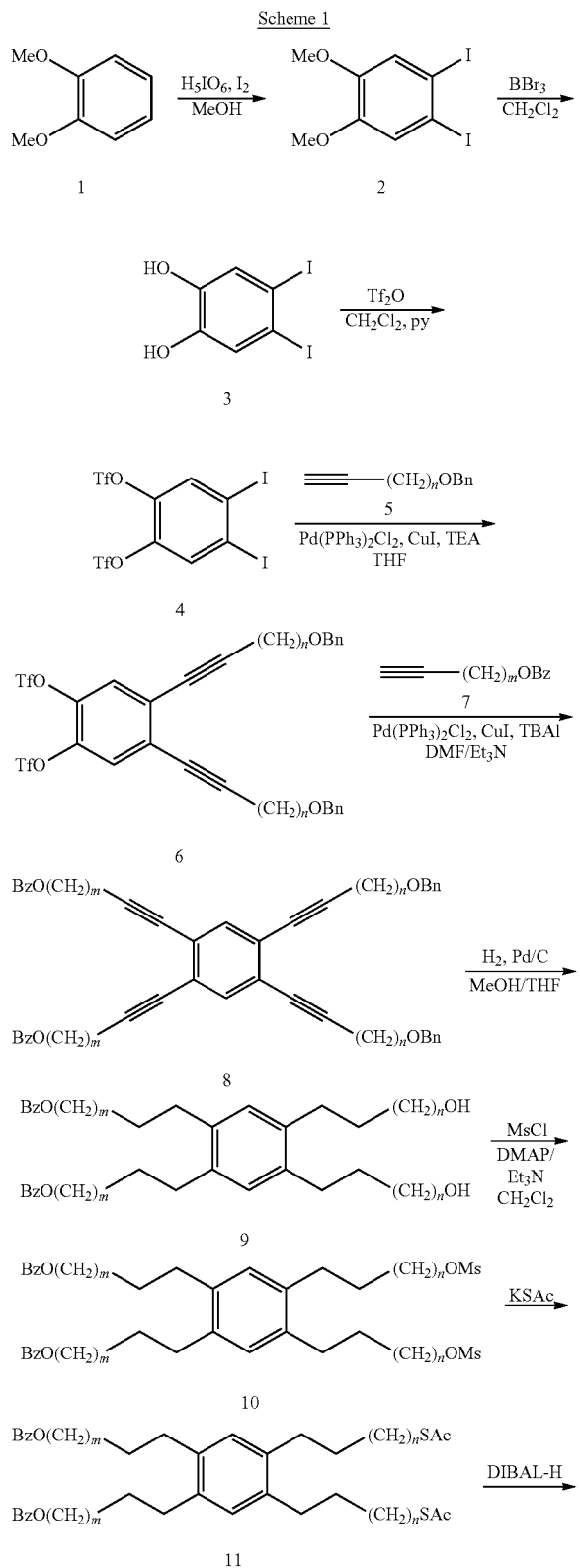

A series of compounds of formula 17 are prepared by the methods outlined in scheme 2 (where m of formulas 13-17 corresponds to appropriate values that would afford compounds of the invention). An alkeneol 13 is treated with $PPh_3$ and N-chlorosuccinimide in THF to afford chloride 14, which undergoes cross-metathesis in the presence of Grubbs $2^{nd}$ generation catalyst and methylacrylate to provide 15. The enoate is then reductively dimerized in the presence of $SmI_2$ to form product 16 as a mixture of stereoisomers. Displacement of the chlorides with KSAc and global reduction with DIBAl—H affords the final compound 17.

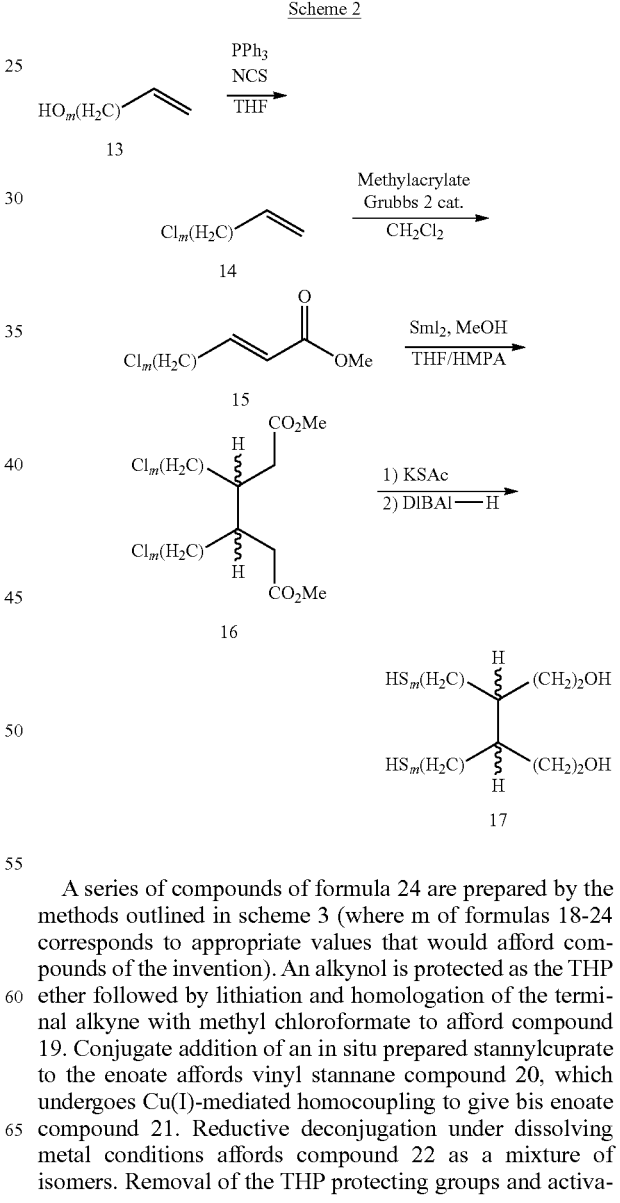

A series of compounds of formula 24 are prepared by the methods outlined in scheme 3 (where m of formulas 18-24 corresponds to appropriate values that would afford compounds of the invention). An alkynol is protected as the THP ether followed by lithiation and homologation of the terminal alkyne with methyl chloroformate to afford compound 19. Conjugate addition of an in situ prepared stannylcuprate to the enoate affords vinyl stannane compound 20, which undergoes Cu(I)-mediated homocoupling to give bis enoate compound 21. Reductive deconjugation under dissolving metal conditions affords compound 22 as a mixture of isomers. Removal of the THP protecting groups and activation as the methanesulfonate gives compound 23. Displacement of the sulfonate groups with KSAc and global reduction with DIBAl—H provides the final compound 24.

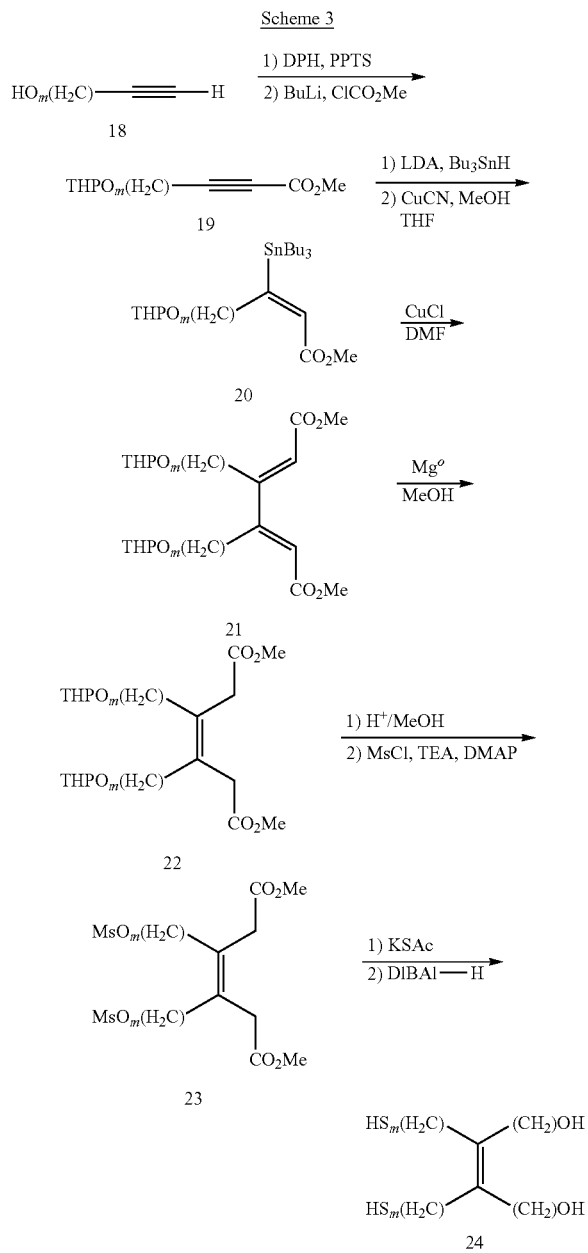

Methods

The compounds described herein are ideally suited for several applications, including biomaterial fabrication, corrosion resistance, lithographic patterning and microelectronics fabrication. This new class of compounds can also be used to create highly stable self-assembled monolayers (SAMs) on metal and semiconductor surfaces which can be used to fabricate electrochemical biosensors.

The term "self-assembled monolayer" (SAM), as used herein, refers to a relatively ordered assembly of molecules (including compounds of Formula I or II) adsorbed on a surface, in which the molecules are oriented approximately parallel to each other and roughly perpendicular to the surface. Each of the molecules preferably includes a functional group that adheres to the surface, and a portion that interacts with neighboring molecules in the monolayer to form the relatively ordered array.

Preferably, all of the species that participate in the SAM include a functionality that binds, optionally covalently, to the surface, such as a thiol which will bind covalently to a metal, such as gold, surface. A self-assembled monolayer on a surface, in accordance with the invention, can be composed of a mixture of species (e.g. thiol species when gold is the surface) that can present (expose) essentially any chemical or biological functionality. For example, they can include species terminating in a binding partner of an affinity tag, e.g. terminating in a chelate that can coordinate a metal such as nitrilotriacetic acid which, when in complex with nickel atoms, captures a metal binding tagged-species such as a histidine-tagged binding species.

In some embodiments of the invention, the self-assembled monolayers can be used in a sensor to detect biomolecules in a sample. For example, in one embodiment, one or more biomolecules in a sample, can be detected by (a) providing a component that comprises a self-assembled monolayer comprising a compound of Formula I or II; (b) binding a multivalent cation to the monolayer; (c) capturing a binding partner onto the monolayer, wherein the binding partner comprises a detectable marker and a moiety capable of binding the multivalent cation; (d) exposing the sample to the monolayer component; and (e) detecting a signal from the detectable marker.

As used herein, the word "comprise," or variations such as "comprises" or "comprising," will be understood to imply the inclusion of a stated element or group of elements, but not to the exclusion of any other element or group of elements.

As used herein, a "biomolecule" is any molecule of a type typically found in a biological system, whether such molecule is naturally occurring or the result of some external disturbance of the system (e.g., a disease, poisoning, genetic manipulation, etc.), as well as synthetic analogs and derivatives thereof. Non-limiting examples of biomolecules include amino acids (naturally occurring or synthetic), peptides, polypeptides, glycosylated and unglycosylated proteins (e.g., polyclonal and monoclonal antibodies, receptors, interferons, enzymes, etc.), nucleosides, nucleotides, oligonucleotides (e.g., DNA, RNA, PNA oligos), polynucleotides (e.g., DNA, cDNA, RNA, etc.), carbohydrates, hormones, haptens, steroids, toxins, etc. Biomolecules may be isolated from natural sources, or they may be synthetic.

In some embodiments, the self-assembled monolayer of the invention is composed of a plurality of compounds of Formula I or II, whereby a portion of the compounds are functionalized with a moiety that is capable of binding a multivalent cation. In some embodiments, at least about 5% of the compounds are functionalized with a moiety that is capable of binding a monovalent cation. In other embodiments, at least about 1-5% or about 5-10% or about 20, 30, 35, 40, 45, or 50% of the compounds are functionalized with a moiety that is capable of binding a monovalent cation.

In some embodiments, the SAM-functionalized moiety capable of binding a multivalent cation is a chelating molecule. By the term "chelating molecule" or "chelating agent" is meant a compound that has the ability to bond to a metal ion through two or more atoms of the chelating agent to form a complex or a reaction product. The bonds may be covalent or ionic or a combination thereof. Examples of suitable chelating agents include acidic materials such as ethylenediamine tetraacetic acid, nitrilo triacetic acid and sodium tripolyphosphate. Other suitable chelating agents of the invention include, but are not limited to, chelating agents comprising nitrilotriacetic acid (NT A), 1,4,7-triazacyclononane (TACN), diethylene triamine pentaacetic acid (DTPA), 1,4,7,10-tetraazacyclododecane-1,4,7,10-tetraacetic acid (DOTA), or imidazole moieties. Other suitable chelating agents include, but are not limited to N,N'-di-L-histidylethane-1,2-diamine (Dhen), iminodiacetic acid (IDA), tris(carboxymethyl)ethylenediamine (TED) carboxymethylated aspartic acid (CM-Asp), dipicolylamine (DPA), aminohydroxamine acid, salicylaldehyde, or orthophoserine (OPS).

In some embodiments of the invention, a multivalent cation is attached to the monolayer upon binding to the SAM-functionalized moiety, described above, that is capable of binding a multivalent cation. As used herein, the term "multivalent cation," refers to materials capable of carrying a positive ionic charge of +2 or greater. In some embodiments, the multivalent cation is a divalent or trivalent cation. Nonlimiting examples of "multivalent cationic" materials include alkaline earth metal ions, aluminum ions and heavy metal ions. In some embodiments of the invention, the multivalent cation is nickel, cobalt, or zinc. In some embodiments, the multivalent cation is Zn(II), Co(II)), or Ni(II). In other embodiments of the invention, the multivalent cation is Fe(III), Cu(II), V(III), W(IV), Ca(II), Al(III) or Yb(III).

In some embodiments of the invention, a binding partner is captured onto the monolayer, the binding partner comprising a detectable marker and a moiety capable of binding a multivalent cation. As used herein, term "binding" or "bound" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, anti body/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

Accordingly, as used, herein, a "binding partner" refers to a molecule that can undergo the aforementioned binding with a particular molecule. Biological binding partners are examples. For example, the protein Arah2 (or a peptide epitope therefrom) is a binding partner of anti-peanut antibody IgY, and vica versa. Accordingly, in some embodiments of the invention, the binding partner is a biological binding partner. Suitable binding partners include, for example, peptides, proteins, nucleic acids, glycoproteins, lipids, carbohydrates, hormones and the like. In some embodiments of the invention, the binding partner is a peptide, protein or nucleic acid. In one embodiment, the binding partner is a peptide.

As used herein, a "peptide" is an oligomer in which the monomers are amino acids and which is joined with another peptide through amide bonds, and is alternatively referred to as a polypeptide. Peptides comprise at least two amino acids, and are usually, but not exclusively, less than 50 amino acids in length According to the invention, the peptide probes described herein may be partially or fully synthetic, and may, for example, comprise one or more of the following moieties: cyclized residues or peptides, multimers of peptides, labels, and/or other chemical moieties. The peptide probes of the invention described herein may interact with, but are not limited to, antibodies, or antigens such as specific proteins, nucleic acids, lipids, or polysaccharides. In some embodiments, the peptide probes are generally specific for the target biomolecule to be detected. These peptides can be used as probes for antigens detection when the use of specific antibodies is not necessary.

According to the invention, the binding partner is labeled with a detectable marker directly or indirectly, so that the binding partner-biomolecule complex can be detected. According to the invention, a "detectable marker" is not restricted to a special type of detection marker, such as biochemical detection marker, but includes any residue known in the art which is suitable for detection. In some embodiments of the present invention, the binding partner defined above comprises a detectable marker that is a fluorescent marker, radioactive marker, or a redox-active marker. In some embodiments, the detectable marker includes, but is not limited to, a His-tag (detectable through its affinity to anti-His antibodies or with fluorescent probes bearing metal ions), glutathione transferase (GST) (detectable through its high affinity for glutathione), Flag-tag (detectable using antibodies against the flag sequence: N-DYKDDDDK-C), biotin (detectable with anti-biotin antibodies or avidinistrepavidine-tagged detection strategies such as horseradish peroxidase, alkaline phosphatase or fluorescent probes), Ha-tag (detectably through its affinity for anti-HA antibody), and Myc-tag (detectable with an antibody against the Myc epitope). In some embodiments of the invention, the detectable marker is a redox molecule. The term "redox molecule," "redox indicator," or "redox dye" denotes a molecule which is capable of accepting or donating an electron thereby changing its redox state. The change in redox state can be measured spectrophotometrically. Non-limiting examples of suitable redox molecules include redox indicators such as thionine, brilliant cresyl blue, methylene blue (3,7-bis(Dimethylamino)-phenothiazin-5-ium chloride) and benzyl viologen. Other suitable redox molecules include, for example, alizarin brilliant blue, 2,6-dichlorophenolindophenol, gallocyanine, new methylene blue, N,N-dimethyl-disulphonated thionine, phenazine ethosulphate, resorufin, safranine-O, phenothiazinone, toluidine blue-O, nile blue, ferrocene, anthraquinone, Ru(bpy)$_3$, Os(bpy)$_3$, Co(bpy)$_3$, thidiazuron (TDZ), 6-benzylaminopurine, and derivatives thereof. In one embodiment of the invention, the redox indicator is methylene blue.

According to the invention, at least one target biomolecule in a specimen can be quantified by counting the signals of the detectable marker directly or indirectly. When the labeled marker is a redox molecule, dye, fluorophore or radioisotope, the presence of the biomolecule can be quantified directly by counting the signal of the marker.

In some embodiments, the binding partner is also functionalized with a moiety capable of binding multivalent cations. In this embodiment, the moiety capable of binding a multivalent cation includes chelating molecules. Here, the term "chelating molecule" or "chelating agent" includes any compound that has the ability to bond to a metal ion through two or more atoms of the chelating agent to form a complex or a reaction product. The bonds may be covalent or ionic or a combination thereof. In some embodiments, the chelating agent comprises one or more amino acids. For example, in some embodiments, the chelating agent can comprise one or more histidine amino acids. In other embodiments of the invention, the chelating agent is a histidine (His) tag such as a hexahistidine moiety. In other embodiments of the invention, the chelating agent include compounds such as ethylenediamine tetraacetic acid, nitrilo triacetic acid and sodium tripolyphosphate. Other suitable chelating agents of the invention include, but are not limited to, chelating agents comprising nitrilotriacetic acid (NT A), 1,4,7-triazacyclononane (TACN), diethylene triamine pentaacetic acid (DTPA), 1,4,7,10-tetraazacyclododecane-1,4,7,10-tetraacetic acid (DOTA), or imidazole moieties.

In some embodiments, the SAM contains thiolated molecules that are adsorbed to a metal surface via a thiol-metal bond. In this embodiment, the metal surface can include a gold surface. The sulfur/gold interaction is very stable and allows for the preparation of SAMs containing thiol functional groups even in the presence of a variety of other substituents. In some embodiments of the invention, the SAM can be formed on metal, metal alloy, or semiconductors surfaces, including Pt, Cu, Pd, Ni, Ir, Ru, Ag, Hg, Zn, Ge, HgTe, AgS, AuAg, AuCu, CdS, FePt, GaAs, InP, PbS, PdAg, ZnSe, ZnS, CdSe, and stainless steel surfaces. Suitable surfaces are described in Chemical Reviews, 2005, 105(4) 1107, which is incorporated by reference herein in its entirety.

In some embodiments, the SAM contains at least one silanol functional group (or a precursor such as an alkoxysilane that readily liberates a silanol upon exposure to moisture) that is capable of forming a covalent linkage to a siloxane or similar surface. The SAM can be appended using silane group with a wide range of substrates, including silicon-based materials (e.g., silicon wafers, silicon nanowires), diamond-based materials (e.g., boron-doped diamond substrates), borosilicate and quartz substrates, transparent conducting electrode materials (e.g., indium tin oxide), and carbon-based materials (e.g., glassy carbon, carbon nanotubes). In some embodiments, the SAM contains at least one basic nitrogen in the form of an amine, imidazole, triazole, or the like, that can be absorbed to a metal surface.

In some embodiments, a SAM is prepared by adsorbing the compound of Formula I or II onto a metal surface. A surface-bound SAM containing a terminal reactive group (such as a chelating agent) can be used as platform onto which one can couple different peptide probes to the monolayer.

In some embodiments, the monolayer can be formed by adsorbing a compound of Formula I or II, functionalized with a chelating agent (such as imidazole), onto a gold disk electrode, followed by subsequent adsorption of a passivating diluent, such as 8-mercapto-1-octanol (C8-OH). The mixed monolayer is then exposed to metal ions for direct coordination with the surface-immobilized imidazole ligands. Various cations are known to coordinate with imidazole ligands, such as metal ions zinc (Zn(II)), cobalt (Co(II)), and nickel (Ni(II)). A histidine tagged methylene blue ($His_6$-MB) is then introduced to the metal-containing monolayer. Alternating current voltammetry (ACV) can then be used to characterize SAM by analysing the AC voltammetric peak consistent with the formal potential of the MB redox label.

In some embodiments, the probe immobilization strategy described herein is not permanent and the attached probes can be effectively displaced by excess free ligands in the solution. The displacement or "regeneration" step provides a SAM that can be used multiple times for different sensing applications, such as microfluidic-based sensing systems.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

All reactions were carried out in flame dried glassware under an atmosphere of dry nitrogen. Solvents were used as purchased with the exception of THF and $CH_2Cl_2$, which were distilled from $Na/Ph_2CO$ and $CaH_2$, respectively. Thin layer chromatography (TLC) was performed on 0.25 mm hard-layer silica G plates; developed plates were visualized by UV lamp and/or by staining with vanillin, 1% aq. $KMnO_4$ (for unsaturated compounds), $I_2$, or phosphomolybdic acid. NMR spectra were obtained in $CDCl_3$ (using residual $CHCl_3$ δ=7.286 ppm) at 300, 400, 500, or 600 MHz for $^1H$ NMR spectra or at 75, 100, 125, or 150 MHz for $^{13}C$ spectra, as indicated below. Infrared spectra were recorded as neat ATR films with selected absorbance reported in wavenumbers ($cm^{-1}$).

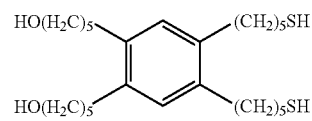

Example 1

5,5'-(4,5-bis(5-mercaptopentyl)-1,2-phenylene)bis(pentan-1-ol)

Step 1

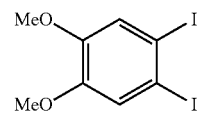

1,2-diiodo-4,5-dimethoxybenzene

To a flame-dried round-bottomed flask equipped with a short air condenser was added $H_5IO_6$ (0.41 equiv., 25.6 mmol, 5.84 g) and methanol (36 mL). The mixture was stirred at rt and $I_2$ (0.8 equiv., 50.2 mmol, 12.76 g) was added. The reaction was stirred vigorously for 10 min, after which 1,2-dimethoxybenzene (1 equiv., 63 mmol, 8.7 g, 8.0 mL) was added in one portion via syringe. The reaction was then heated to 70° C. for 5 h, producing a slurry comprising white solid. The hot solution was poured into dilute aqueous $Na_2S_2O_5$ (100 mL) and cooled to rt. The solid was collected by filtration through a glass frit and washed with two 30 mL portions of cold methanol and dried in vacuo to afford 1,2-diiodo-4,5-dimethoxybenzene (21.07 g, 54 mmol, 86%) as a white solid. TLC $R_f$=0.49 (20% EtOAc/Hex); Melting point 134.5-136.0° C. (134° C. lit.[7]). $^1H$ NMR (600 MHz): δ 7.25 (s, 2H), 3.85 (s, 6H); $^{13}C$ NMR (150 MHz): δ 149.6, 121.7, 96.1, 56.2.

Step 2

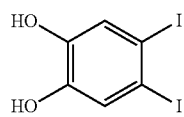

4,5-diiodobenzene-1,2-diol

To a flame-dried round-bottomed flask was added 1,2-diiodo-4,5-dimethoxybenzene (1 equiv., 10 mmol, 3.90 g). The system was evacuated under nitrogen (3×), $CH_2Cl_2$ (70 mL) was added, and the resulting solution was cooled to 0° C. $BBr_3$ (2.5 equiv., 25 mmol, 25 mL of a 1.0 M solution in $CH_2Cl_2$) was then added via syringe pump over 20 min. The reaction was stirred at 0° C. for 4 h then quenched with $H_2O$ (50 mL). The separated aqueous layer was then extracted with $Et_2O$ (2×75 mL). The combined organic layers were dried with $MgSO_4$, filtered through silica, and concentrated in vacuo to afford 1,2-dihydroxy-4,5-diiodobenzene (3.61 g, 9.99 mmol, quantitative) as an off-white solid. TLC $R_f$=0.50 (50% EtOAc/Hex); Melting point 116.0-116.5° C.; $^1H$ NMR (400 MHz, acetone-$d_6$): δ 8.48 (bs, 2H), 7.38 (s, 2H). $^{13}C$ NMR (150 MHz, acetone-$d_6$): δ 146.5, 125.6, 93.7.

Step 3

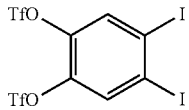 [SMILES: O=S(=O)(Oc1cc(I)c(I)cc1OS(=O)(=O)C(F)(F)F)C(F)(F)F]

4,5-diiodo-1,2-phenylene bis(trifluoromethanesulfonate)

To a flame-dried round-bottomed flask was added 1,2-dihydroxy-4,5-diiodobenzene (1 equiv., 7.85 mmol, 2.84 g), $CH_2Cl_2$ (55 mL), and pyridine (5 equiv., 39 mmol, 3.10 g, 3.16 mL). The solution was cooled to 0° C. and $Tf_2O$ (2.2 equiv., 17.3 mmol, 4.88 g, 2.91 mL) was added dropwise via syringe over 10 min. The reaction was stirred for 6 h while warming to ambient temperature, then cooled to 0° C. and quenched with $H_2O$ (30 mL). The separated aqueous layer was extracted with $CH_2Cl_2$ (2×30 mL). The combined organic layers were dried with $MgSO_4$ and filtered through a tall pad of silica. The pad was washed carefully with $CH_2Cl_2$ to avoid the elution of impurities, and the filtrate was concentrated in vacuo to afford 4,5-diiodo-1,2-phenylene bis(trifluoromethanesulfonate) (4.90 g, 7.82 mmol, quantitative) as an off-white solid. The product is optionally purified by column chromatography (10% EtOAc/Hex). TLC $R_f$=0.60 (10% EtOAc/Hex); Melting point 46.5-47.7° C.; $^1H$ NMR (400 MHz): δ 7.91 (s, 2H); $^{13}C$ NMR (100 MHz): δ 139.6, 133.4, 118.5 (q, $J_{C,F}$=321.0 Hz), 108.0. FTIR: 1429, 1335, 1215, 1125, 1105, 868, 788, 745, 689 $cm^{-1}$. HRMS-ESI: calc. for $C_8H_2F_6I_2NaO_6S_2$ $(M+Na)^+$: 648.7184; found: 648.7164.

Step 4

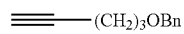

((pent-4-yn-1-yloxy)methyl)benzene

To a flame-dried round-bottomed flask was added NaH (2 equiv., 47.6 mmol, 1.9 g of a 60% dispersion in mineral oil). The solid was washed with hexanes (15 mL), THF (95 mL) was added and the suspension was cooled to 0° C. Pentynol (1 equiv., 23.8 mmol, 2.0 g) was added drop wise in THF (5 mL), followed by drop wise addition of BnBr (0.92 equiv., 21.9 mmol, 2.60 mL). The reaction was warmed to ambient temperature over 16 h, quenched with saturated aqueous $NH_4Cl$ (25 mL), and diluted with water (20 mL). The organic layer was extracted with EtOAc (2×40 mL), washed with brine (40 mL) and dried with $Na_2SO_4$. Product isolation was achieved by concentration in vacuo and purification by flash column chromatography to afford ((pent-4-yn-1-yloxy)methyl)benzene (3.60 g, 20.7 mmol, 94%). TLC $R_f$=0.41 (5% EtOAc/Hex); $^1$HNMR (300 MHz): δ 7.29-7.44 (5H), 4.55 (s, 2H), 3.61 (t, 2H, J=6.2 Hz), 2.36 (td, 2H, J=7.1, 2.6 Hz), 1.97 (t, 1H, J=2.6 Hz), 1.81-1.93 (m, 2H). $^{13}C$NMR (75 MHz): δ 138.5, 128.4, 127.63, 127.58, 84.0, 73.0, 68.7, 68.5, 28.7, 15.3.

Step 5

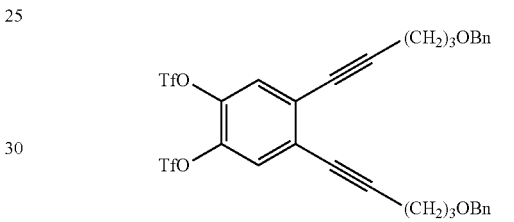

4,5-bis(5-(benzyloxy)pent-1-yn-1-yl)-1,2-phenylene bis(trifluoromethanesulfonate)

A flame-dried 20 mL vial fitted with a screw-cap septa was charged with $Pd(PPh_3)_2Cl_2$ (0.06 equiv., 0.12 mmol, 84 mg), CuI (0.12 equiv., 0.24 mmol, 45.6 mg), and 4,5-diiodo-1,2-phenylene bis(trifluoromethanesulfonate) (1 equiv., 2 mmol, 1.25 g). The vessel was evacuated and backfilled with nitrogen (3×), followed by the sequential addition of THF (4 mL), $Et_3N$ (3 equiv., 6 mmol, 0.85 mL), and ((pent-4-yn-1-yloxy)methyl)benzene (2.3 equiv., 4.6 mmol, 802 mg) in THF (1 mL). The reaction was stirred for 3 h at rt, filtered through a pad of silica and concentrated in vacuo. Purification by flash chromatography (step gradient from Hex to 10% EtOAc/Hex) afforded 4,5-bis(5-(benzyloxy)pent-1-yn-1-yl)-1,2-phenylene bis(trifluoromethanesulfonate) (1.14 g, 1.59 mmol, 79%). TLC $R_f$=0.27 (10% EtOAc/Hex); $^1$HNMR (600 MHz): δ 7.42 (s, 2H), 7.27-7.39 (10H), 4.56 (s, 4H), 3.65 (t, 4H, J=6.0 Hz), 2.62 (t, 4H, J=7.1 Hz), 1.92-1.98 (m, 4H); $^{13}C$NMR (150 MHz): δ 138.8, 138.3, 128.4, 128.2, 127.59, 127.56, 126.3, 121.7, 119.6, 117.5, 115.3, 98.1, 77.4, 73.0, 68.5, 28.6, 16.5; FTIR: 2859, 2230, 1489, 1433, 1210, 1178, 1135, 1080, 732 $cm^{-1}$; HRMS-ESI: calc. for $C_{32}H_{28}F_6O_8S_2Na$ $(M+Na)^+$: 741.1027; found: 741.1039.

Step 6

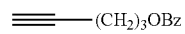

pent-4-yn-1-yl benzoate

To a flame-dried round-bottomed flask was added pentynol (1 equiv., 24 mmol, 2.0 g) and CH$_2$Cl$_2$ (80 mL). The solution was cooled to 0° C. and BzCl (1.2 equiv., 28 mmol, 3.3 mL) was added dropwise, followed by DMAP (0.1 equiv., 2.4 mmol, 300 mg), and Et$_3$N (7 mL). The reaction was warmed to ambient temperature over 12 h, quenched with 2N HCl (10 mL), extracted with EtOAc (2×40 mL), washed with brine (40 mL) and dried over Na$_2$SO$_4$. The purified product was isolated by concentrating in vacuo and purifying by flash chromatography (2.5% EtOAc/Hex) to afford pent-4-yn-1-yl benzoate (4.02 g, 21.4 mmol, 89%). TLC R$_f$=0.57 (10% EtOAc/Hex); $^1$HNMR (600 MHz): δ 8.03-8.07 (2H), 7.53-7.60 (1H), 7.42-7.48 (2H), 4.44 (t, 2H, J=6.1 Hz), 2.40 (td, 2H, J=7.3, 2.7 Hz), 1.98-2.05 (overlapping signals, 3H); $^{13}$CNMR (150 MHz): δ166.5, 132.9, 130.3, 129.6, 128.3, 83.0, 69.1, 63.4, 27.7, 15.4.

Step 7

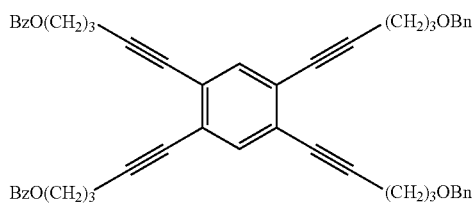

(4,5-bis(5-(benzyloxy)pent-1-yn-1-yl)-1,2-phenylene)bis(pent-4-yne-5,1-diyl)dibenzoate A flame-dried 20 mL vial fitted with a screw-cap septa was charged with Pd(PPh$_3$)$_2$Cl$_2$ (0.12 equiv., 0.18 mmol, 127 mg), CuI (0.30 equiv., 0.45 mmol, 89.4 mg), and Bu$_4$NI (3 equiv., 4.5 mmol, 1.65 g). The vessel was evacuated and backfilled with nitrogen 3×, followed by the addition of 4,5-Bis(5-benzyloxypent-1-yn-1-yl)-1,2-phenylene bistrifluoromethanesulfonate in a 5:1 mixture of DMF/Et$_3$N (7 mL). The mixture was stirred for 5 min at rt, and 5-benzyloxypentyne (4.1 equiv., 6.1 mmol, 980 mg) was added in 1.5 ml of 5:1 DMF/Et$_3$N. The reaction was placed in a 70° C. oil bath for 5.5 h, cooled to rt, and diluted with 1:1 CH$_2$Cl$_2$/hexanes (40 mL). The solution was washed with H$_2$O (2×20 mL), 1N HCl (40 mL), and brine (40 mL) and dried with MgSO$_4$. The product was isolated by concentrating the crude product in vacuo, and purifying by flash chromatography (15% EtOAc/Hex) to afford (4,5-bis(5-(benzyloxy)pent-1-yn-1-yl)-1,2-phenylene)bis(pent-4-yne-5,1-diyl)dibenzoate (930 mg, 1.17 mmol, 79%). TLC R$_f$=0.39 (20% EtOAc/Hex); $^1$HNMR (600 MHz): δ 8.04-8.10 (4H), 7.54-7.60 (2H), 7.42-7.47 (4H), 7.39-7.41 (2H), 7.33-7.38 (8H), 7.27-7.31 (2H), 4.55 (s, 4H), 4.53 (t, 4H, J=6.3 Hz), 3.66 (t, 4H, J=6.2 Hz), 2.70 (t, 4H, J=7.0 Hz), 2.60 (t, 4H, J=7.0 Hz), 2.11 (quint, 4H, 6.6 Hz), 1.94 (quint., 4H, J=6.6 Hz). $^{13}$CNMR (150 MHz): δ 166.5, 138.5, 135.3, 133.0, 130.2, 129.6, 128.38, 128.36, 127.60, 127.56, 125.3, 124.9, 95.0, 93.9, 79.6, 79.1, 73.0, 68.7, 63.7, 28.9, 28.0, 16.7, 16.6; FTIR: 3675, 2988, 2972, 2901, 2229, 1716, 1451, 1394, 1269, 1107, 1068, 1027, 900 cm$^{-1}$; HRMS-ESI: calc. for C$_{54}$H$_{50}$O$_6$Na (M+Na)$^+$: 817.3505; found: 817.3503.

Step 8

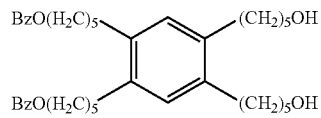

(4,5-bis(5-hydroxypentyl)-1,2-phenylene)bis(pentane-5,1-diyl)dibenzoate (4,5-bis(5-(benzyloxy)pent-1-yn-1-yl)-1,2-phenylene)bis(pent-4-yne-5,1-diyl)dibenzoate (1 equiv., 1.11 mmol, 885 mg) was dissolved in 10 mL of 1:1 Methanol/THF. The mixture is equally partitioned among 5 straight-walled hydrogenation vials containing 20 mg of 10% Pd/C EtOAc. The vials were placed in a hydrogenation chamber and reacted at 40° C. and 30 psi H$_2$ for 18 h. The individual reactions were combined and filtered through a plug of Celite, concentrated in vacuo, and purified via flash chromatography (step gradient, 30% EtOAc/Hex to 100% EtOAc) to afford 4,5-bis(5-hydroxypentyl)-1,2-phenylene) bis(pentane-5,1-diyl) dibenzoate (253 mg, 0.44 mmol, 40%). TLC R$_f$=0.30 (60% EtOAc/Hex) (~30% of the saturated dibenzoate derivative and ~10% of the saturated, monobenzoate derivative were also isolated. These compounds could be resubjected to the reaction conditions to provide additional product); $^1$HNMR (600 MHz): δ 8.04-8.10 (4H), 7.54-7.61 (2H), 7.42-7.50 (4H), 6.94 (s, 2H), 4.36 (t, 4H, J=6.7 Hz), 3.67 (t, 4H, J=6.6 Hz), 2.53-2.68 (8H), 1.80-1.91 (6H), 1.53-1.72 (16H), 1.44-1.51 (4H); $^{13}$CNMR (150 MHz): δ 166.7, 137.6, 137.3, 132.8, 130.4, 129.9, 129.5, 128.3, 65.0, 62.7, 32.5, 32.21, 32.15, 31.2, 30.9, 28.6, 26.1, 25.8; FTIR: 3776, 2988, 2972, 2901, 1717, 1334, 1271, 1067, 1057, 1028 cm$^{-1}$; HRMS-ESI: calc. for C$_{40}$H$_{54}$O$_6$Na (M+Na)$^+$: 653.3818; found: 653.3823.

Step 9

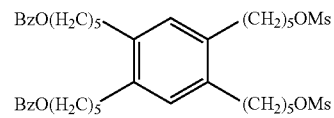

(4,5-bis(5-((methylsulfonyl)oxy)pentyl)-1,2-phenylene)bis(pentane-5,1-diyl)dibenzoate To a flamed-dried 20 mL vial fitted with a screw-cap septa was added (4,5-bis(5-hydroxypentyl)-1,2-phenylene)bis (pentane-5,1-diyl)dibenzoate (1 equiv., 0.34 mmol, 215 mg), CH$_2$Cl$_2$ (4 mL), and Et$_3$N (4 equiv., 1.36 mmol, 0.19 mL). The mixture was cooled to 0° C. and DMAP (0.1 equiv., 0.034 mmol, 4.2 mg) was added followed by the dropwise addition of MsCl (3 equiv., 1.02 mmol, 0.08 mL). The reaction was warmed to ambient temperature over 14 h at which time the reaction was then quenched with sat. aq. NaHCO$_3$ (10 mL). The organic and aqueous layers were separated and the aqueous layer was extracted with CH$_2$Cl$_2$ (3×10 mL). The combined organic layers were washed with water (20 mL), dried with Na$_2$SO$_4$, concentrated in vacuo, and purified by flash chromatography (45% EtOAc/Hex) to afford (4,5-bis(5-((methylsulfonyl)oxy)pentyl)-1,2-phenylene)bis(pentane-5,1-diyl)dibenzoate (294 mg, 0.37 mmol, 91%). TLC R$_f$=0.27 (40% EtOAc/Hex); $^1$HNMR (600 MHz): δ 8.01-8.11 (4H), 7.54-7.62 (2H), 7.46 (t, 4H, J=7.6), 6.92 (s, 2H), 4.35 (t, 4H, J=6.6 Hz), 4.26 (t, 4H, J=6.6 Hz), 3.02 (s, 6H), 2.60 (bt, 4H, J=8.0 Hz), 2.57 (bt, 4H, J=8.0), 1.77-1.88 (8H), 1.48-1.70 (16H). $^{13}$CNMR (600 MHz): δ 166.7, 137.6, 137.3, 132.9, 130.5, 129.9, 129.5, 128.3, 70.1, 65.0, 37.4, 32.2, 32.1, 31.1, 30.8, 29.1, 28.7, 26.2, 25.6; FTIR: 2937, 1714, 1352, 1272, 1173, 1114, 1070, 944, 908 cm$^{-1}$; HRMS-ESI: calc. for $C_{42}H_{58}O_{10}S_2Na$ (M+Na)$^+$: 809.3369; found: 809.3367.

Step 10

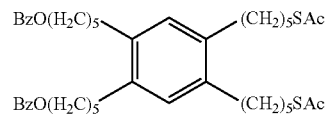

(4,5-bis(5-(acetylthio)pentyl)-1,2-phenylene)bis(pentane-5,1-diyl)dibenzoate

To a flame-dried 8 mL vial fitted with screw-top cap was added 4,5-bis(5-((methylsulfonyl)oxy)pentyl)-1,2-phenylene)bis(pentane-5,1-diyl)dibenzoate (1 equiv., 0.282 mmol, 222 mg) and DMF (2.5 mL). The mixture was cooled to 0° C. and potassium thioacetate (3 equiv., 0.85 mmol, 97 mg) was added. The reaction was warmed to ambient temperature over 14 h at which time the reaction was diluted with Et$_2$O (20 mL) and water (10 mL). The organic and aqueous layers were separated and the organic layer was washed with sat. aq. NaHCO$_3$ (3×10 mL), dried with Na$_2$SO$_4$. The crude product was then concentrated in vacuo, and purified by flash chromatography (10% EtOAc/Hex) to afford (4,5-bis(5-(acetylthio)pentyl)-1,2-phenylene)bis(pentane-5,1-diyl)dibenzoate (170 mg, 0.228 mmol, 81%); TLC R$_f$=0.32 (15% EtOAc/Hex); $^1$HNMR (600 MHz): δ 8.07 (d, 4H, J=7.3 Hz), 7.58 (t, 2H, J=7.4 Hz), 7.46 (t, 4H, J=7.8 Hz), 6.92 (s, 2H), 4.36 (t, 4H, J=6.7 Hz), 2.90 (t, 4H, J=7.3 Hz), 2.60 (bt, 4H, J=7.9 Hz), 2.55 (bt, 4H, J=7.9 Hz), 2.35 (s, 6H), 1.80-1.89 (8H), 1.54-1.70 (8H), 1.44-1.51 (4H); $^{13}$CNMR (150 MHz): δ 195.9, 166.7, 137.5, 137.3, 132.8, 130.5, 129.9, 129.5, 128.3, 65.0, 32.3, 32.2, 31.1, 30.9, 30.7, 29.5, 29.1, 28.7, 26.3; FTIR: 3684, 3675, 2988, 2972, 2901, 1717, 1688, 1406, 1394, 1383, 1230, 1057, 1028 cm$^{-1}$; HRMS-ESI: calc. for $C_{44}H_{58}O_6S_2Na$ (M+Na)$^+$: 769.3573; found: 769.3568.

Step 11

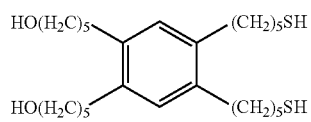

5,5'-(4,5-bis(5-mercaptopentyl)-1,2-phenylene)bis(pentan-1-ol)

A flame-dried 8 mL vial fitted with a screw-top cap was charged with (4,5-bis(5-(acetylthio)pentyl)-1,2-phenylene)bis(pentane-5,1-diyl)dibenzoate (1 equiv., 0.193 mmol, 144 mg) and THF (2.5 mL). i-Bu$_2$AlH (DIBAl—H) (12 equiv., 2.3 mmol, 1.55 mL of a nominally 1.5 M solution in toluene) was added dropwise. The reaction was stirred at rt for 2.5 h, cooled to 0° C., and quenched by the careful addition of 4 mL 2N HCl. The solution was diluted with water (10 mL), extracted with Et$_2$O (3×10 mL), washed with brine (10 mL), and dried over Na$_2$SO$_4$. The crude product was then concentrated in vacuo and purified via flash chromatography (50% EtOAc/Hex) to afford 5,5'-(4,5-bis(5-mercaptopentyl)-1,2-phenylene)bis(pentan-1-ol) (74 mg, 0.163 mmol, 84%). TLC R$_f$=0.19 (45% EtOAc/Hex); $^1$HNMR (600 MHz): δ 6.92 (s, 2H), 3.68 (t, 4H, 6.6 Hz), 2.53-2.61 (12H), 1.56-1.72 (18H), 1.45-1.53 (8H), 1.37 (t, 2H, J=7.9 Hz); $^{13}$CNMR (150 MHz): δ 137.6, 137.4, 129.9, 62.9, 33.9, 32.6, 32.3, 32.2, 31.2, 30.8, 28.5, 25.9, 24.6; FTIR: 3353, 2930, 2857, 2358, 2338, 1775, 1460, 1143 cm$^{-1}$; HRMS-ESI: calc. for $C_{26}H_{46}O_2S_2Na$ (M+Na)$^+$: 477.2837; found: 477.2821.

Example 2

3,4-Bis(8-mercaptooctyl)hexane-1,6-diol

Step 1

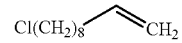

10-Chlorodecene

To a flame-dried round-bottomed flask was added PPh$_3$ (1.1 equiv, 27.5 mmol, 7.21 g) and THF (65 mL). N-chlorosuccinimide (1.1 equiv, 27.5 mmol, 3.67 g) was dissolved in THF (50 mL) and added dropwise. The mixture was stirred for 5 min, and 9-decen-1-ol (1 equiv, 25 mmol, 3.91 g) was added dropwise in THF (30 mL). After 9 h, the volatile components of the reaction were evaporated and hexanes (100 mL) and H$_2$O (50 mL) were added. The liquid was decanted and the resulting solid was washed with hexanes. The aqueous layer was collected and extracted with hexanes (2×50 mL). The combined organic layers were washed sequentially with bleach (30 mL) and brine (50 mL). The crude product was filtered through a pad of silica (which was washed with ~400 mL of hexanes) and concentration in vacuo to afford 10-chlorodecene (3.48 g, 20 mmol, 80%), which was deemed pure by NMR and used without further purification. TLC R$_f$=0.87 (5% EtOAc/Hex); $^1$HNMR (400 MHz): δ 5.84 (ddt, 1H, J=17.4, 10.3, 6.7 Hz), 5.02 (ddd, 1H, J=17.4, 2.0, 3.6 Hz), 4.93-4.98 (m, 1H), 3.56 (t, 2H, J=6.5 Hz), 2.02-2.12 (m, 2H), 1.74-1.84 (2H), 1.27-1.50 (10H); $^{13}$CNMR (100 MHz): δ 139.2, 114.2, 45.2, 33.8, 32.7, 29.3, 29.0, 28.88, 28.85, 26.88.

Step 2

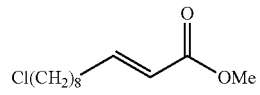

(E)-Methyl 11-chloroundec-2-enoate

To a flame-dried round-bottomed flask, evacuated and backfilled with nitrogen (3×), was added 10-chlorodecene (1 equiv, 16 mmol, 2.79 g), methyl acrylate (25 equiv, 395 mmol, 36 mL), and CH$_2$Cl$_2$ (140 mL). Grubbs 2 catalyst (0.031 equiv, 0.48 mmol, 416 mg) was dissolved in CH$_2$Cl$_2$ (15 mL) and added to the reaction mixture in one portion.

The reaction was stirred for 4 h, concentrated in vacuo, and purified by flash column chromatography (3% EtOAc/Hex) to afford (E)-methyl 11-chloroundec-2-enoate (3.14 g, 13.6 mmol, 85%). TLC $R_f$=0.30 (5% EtOAc/Hex); $^1$HNMR (300 MHz): δ 6.99 (dt, 1H, J=15.6, 7.0 Hz), 5.84 (dt, 1H, J=15.7, 1.5 Hz), 3.75 (s, 3H), 3.55 (t, 2H, J=6.8 Hz), 2.22 (qd, 2H, J=7.3, 1.4 Hz), 1.72-1.85 (m, 2H), 1.26-1.55 (10H); $^{13}$CNMR (75 MHz): δ 167.2, 149.6, 120.9, 51.4, 45.1, 32.6, 32.2, 29.2, 29.0, 28.7, 27.9, 26.8; FTIR: 2928, 2856, 1722, 1657, 1435, 1270, 1195, 1174, 1041, 979, 720 cm$^{-1}$; HRMS-ESI: calc. for $C_{12}H_{21}ClNaO_2$ (M+Na)$^+$: 255.1128; found: 255.1118.

Step 3

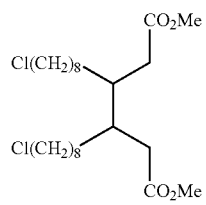

Dimethyl 3,4-bis(8-(chloro)octyl)hexanedioate

To a flame-dried round-bottomed flask, evacuated and backfilled with nitrogen (3×) and equipped with a dropping funnel was added (E)-methyl 11-chloroundec-2-enoate (1 equiv, 11.9 mmol, 2.77 g), THF (25 mL), MeOH (0.9 mL), and HMPA (25 mL). SmI$_2$ (2.1 equiv, 25 mmol, 250 mL of a nominally 0.1 M solution in THF) was added rapidly in one portion via dropping funnel. The reaction was stirred for 0.5 h, quenched by the dropwise addition of 2 N HCl (20 mL), and diluted with H$_2$O (100 mL) and Et$_2$O (100 mL). The layers were separated, and the aqueous layer was extracted with Et$_2$O (2×50 mL). The combined organic layers were washed with brine (2×50 mL), dried with MgSO$_4$, concentrated in vacuo, and purified by flash column chromatography (step-wise gradient 5% to 8% EtOAc/Hex) to afford Dimethyl 3,4-bis(8-(chloro)octyl)hexanedioate (1.76 g) as a mixture of stereoisomers and an unidentified impurity. TLC $R_f$=0.43 (10% EtOAc/Hex).

The mixture can be used directly in the next reaction. Alternatively, the impurity can be removed by reacting the product (47 mg) with NaBH$_4$ (3.8 mg) in THF (1 mL). After 3.5 h, the reaction was quenched with 3 mL H$_2$O, extracted with CH$_2$Cl$_2$ (3×5 mL), dried with Na$_2$SO$_4$, concentrated in vacuo, and purified by flash column chromatography (10% EtOAc/Hex) to afford purified Dimethyl 3,4-bis(8-(chloro) octyl)hexanedioate (26 mg). TLC $R_f$=0.43 (10% EtOAc/ Hex); $^1$HNMR (300 MHz): δ 3.68 (s, 6H), 3.55 (t, 4H, J=6.8 Hz), 1.91-2.35 (6H), 1.71-1.85 (4H), 1.13-1.50 (24H); $^{13}$CNMR (75 MHz): δ 173.94, 173.88, 51.54, 51.51, 45.14, 37.4, 37.2, 36.2, 35.7, 32.6, 31.5, 30.7, 29.6, 29.3, 28.8, 27.4, 27.3, 26.8; FTIR: 2927, 2855, 1735, 1435, 1251, 1191, 1165, 1016, 722 cm$^{-1}$; HRMS-ESI: calc. for $C_{24}H_{44}Cl_2NaO_4$ (M+Na)$^+$: 489.2514; found: 489.2506.

Step 4

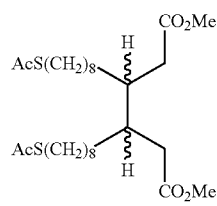

Dimethyl 3,4-bis(8-(acetylthio)octyl)hexanedioate

To a flame-dried 20 mL vial fitted with a screw-top septa cap was charged with pure dimethyl 3,4-bis(8-(chloro)octyl) hexanedioate (1 equiv, 0.46 mmol, 215 mg, mixture of stereoisomers) and DMF (4 mL). KSAc (5 equiv, 2.3 mmol, 263 mg) was added in one portion and the reaction was stirred for 14 h at rt, diluted with Et$_2$O (25 mL), washed with sat. aq. NaHCO$_3$ (2×10 mL), dried with Na$_2$SO$_4$, concentrated in vacuo, and purified by flash column chromatography (step-wise gradient 5% to 10% EtOAc/Hex) to afford Dimethyl 3,4-bis(8-(acetylthio)octyl)hexanedioate (215 mg, 85%). TLC $R_f$=0.32 (10% EtOAc/Hex); $^1$HNMR (300 MHz): δ 3.68 (s, 6H), 2.87 (t, 4H, J=7.3 Hz), 1.92-1.40 (12H), 1.51-1.64 (4H), 1.16-1.41 (24H); $^{13}$CNMR (75 MHz): δ 196.0, 174.0, 173.9, 51.5, 37.4, 37.2, 36.2, 35.7, 31.5, 30.7, 30.6, 29.7, 29.5, 29.4, 29.13, 29.06, 28.8, 27.4, 27.3; FTIR: 2926, 2854, 1736, 1689, 1435, 1353, 1250, 1165, 1133, 1106, 1013, 953 cm$^{-1}$; HRMS-ESI: calc. for $C_{28}H_{50}NaO_6S_2$ (M+Na)$^+$: 569.2947; found: 569.2945.

Stereochemical assignment was made by chiral HPLC analysis of the product mixture (ChiralPak IC, 90:10 Hex: iPrOH, 0.5 mL/min; UV detecation was performed at 254 nm). The racemic (rac) stereoisomer eluted as two peaks at 114 and 119 min; the meso stereoisomer eluted at 142 min. The ratio of meso:rac. was 1.44:1.

Step 5

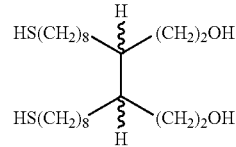

3,4-Bis(8-mercaptooctyl)hexane-1,6-diol

To a flame-dried 20 mL vial fitted with a screw-top septa cap was charged with dimethyl 3,4-bis(8-(acetylthio)octyl) hexanedioate (1 equiv, 0.34 mmol, 187 mg, mixture of stereoisomers) and THF (4.5 mL). DIBAl—H (12 equiv, 4.1 mmol, 2.7 mL of a nominally 1.5 M solution in toluene) was added dropwise. The reaction was stirred for 3 h at rt, quenched by careful addition of 2 N HCl (5 mL), diluted with 10 mL sat. aq. NH$_4$Cl (10 mL), and extracted with Et$_2$O (3×15 mL). The combined organic layers were washed with brine (1×15 mL), dried with Na$_2$SO$_4$, concentrated in vacuo, and purified by flash column chromatography (35% EtOAc/ Hex) to afford rac-3,4-Bis(8-mercaptooctyl)hexane-1,6-diol (41 mg, 30%) and meso-3,4-Bis(8-mercaptooctyl)hexane-1, 6-diol (49 mg, 49%). TLC rac-$R_f$=0.57 (50% EtOAc/Hex), meso-$R_f$=0.38 (50% EtOAc/Hex); rac: $^1$HNMR (400 MHz):

δ 3.60-3.79 (4H), 2.54 (q, 4H, J=7.3 Hz), 1.14-1.68 (38H); $^{13}$CNMR (100 MHz): δ 61.6, 35.8, 34.0, 33.7, 30.7, 30.0, 29.5, 29.1, 28.3, 28.0, 24.6; FTIR: 3323, 2922, 2852, 1463, 1051, 722 cm$^{-1}$; HRMS-ESI: calc. for $C_{22}H_{46}NaO_2S_2$ (M+Na)$^+$: 429.2837; found: 429.2825; meso: $^1$HNMR (400 MHz): δ 3.59-3.76 (4H), 2.54 (q, 4H, J=7.3 Hz), 1.87 (bs, 2H), 1.08-1.68 (36H); $^{13}$CNMR (100 MHz): δ 61.9, 36.7, 34.0, 33.8, 30.7, 30.0, 29.5, 29.1, 28.4, 28.0, 24.7; FTIR: 3329, 2922, 2852, 1463, 1051, 721 cm$^{-1}$; HRMS-ESI: calc. for $C_{22}H_{46}NaO_2S_2$ (M+Na)$^+$: 429.2837; found: 429.2829.

Example 3

(Z)-3,4-bis(8-mercaptooctyl)hex-3-ene-1,6-diol

Step 1

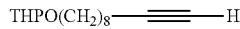

9-Decyn-1-ol tetrahydropyranyl ether

To a flame-dried round-bottomed flask was added 9-decyn-1-ol (1 equiv, 32.4 mmol, 5.00 g), dihydropyran (1.5 equiv, 48.6 mmol, 4.09 g, 4.5 mL), CH$_2$Cl$_2$ (50 mL), and PPTS (0.1 equiv, 3.24 mmol, 800 mg). The reaction was stirred for 16 h at rt and quenched with sat. aq. NaHCO$_3$ (40 mL). The layers were separated and the aqueous layer was extracted with CH$_2$Cl$_2$ (2×20 mL). The combined organic layers were washed with H$_2$O (30 mL), dried with Na$_2$SO$_4$, concentrated in vacuo, and purified by flash column chromatography (5% EtOAc/Hex) to afford 9-Decyn-1-ol tetrahydropyranyl ether (7.55 g, 31.7 mmol, 98%). TLC R$_f$=0.30 (5% EtOAc/Hex); $^1$HNMR (600 MHz): δ 4.55-4.62 (1H), 3.83-3.91 (m, 1H), 3.70-3.78 (m, 1H), 3.48-3.55 (m, 1H), 3.36-3.43 (m, 1H), 2.19 (td, 2H, J$_1$=7.1 Hz, J$_2$=2.6 Hz), 1.95 (t, 1H, J=2.6), 1.80-1.89 (1H), 1.69-1.76 (1H), 1.50-1.63 (8H), 1.28-1.44 (8H); $^{13}$CNMR (150 MHz): δ 98.8, 84.7, 68.1, 67.6, 62.3, 30.8, 29.7, 29.3, 29.0, 28.7, 28.5, 26.2, 25.5, 19.7, 18.4.

Step 2

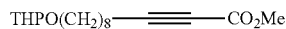

Methyl-11-[(tetrahydro-2H-pyran-2-yl)oxy]-undecynoate

A flame-dried round-bottomed flask was charged with 9-decyn-1-ol tetrahydropyranyl ether (1 equiv, 31.7 mmol, 7.55 g) and THF (40 mL), and cooled to −78° C. n-BuLi (1.1 equiv, 34.9 mmol, 21.8 mL of a nominally 1.6 M solution in hexanes) were added dropwise over 5 min. The reaction was stirred for 30 min at −78° C. and then added to a solution of methyl chloroformate (1.5 eq, 47.6 mmol, 4.50 g, 3.7 mL) in THF (20 mL) dropwise via cannula. The reaction was stirred for 30 min at −78° C., then warmed to rt over 1 h and quenched dropwise with H$_2$O (40 mL). The layers were separated and the aqueous layer was extracted with Et$_2$O (2×25 mL). The combined organic layers were dried with Na$_2$SO$_4$, evaporated in vacuo, and purified by flash column chromatography (step gradient, 5% EtOAc/Hex to 10% EtOAc/Hex) to afford Methyl-11-[(tetrahydro-2H-pyran-2-yl)oxy]-undecynoate (8.50 g, 28.7 mmol, 90%). TLC R$_f$=0.33 (10% EtOAc/Hex) $^1$HNMR (600 MHz): δ 4.55-4.61 (1H), 3.84-3.91 (m, 1H), 3.70-3.78 (m plus ovlp. s, 4H), 3.47-3.54 (m, 1H), 3.39 (dt, 1H, J$_1$=9.6 Hz, J$_2$=6.7 Hz), 2.33 (t, 2H, J=7.1 Hz), 1.80-1.89 (1H), 1.68-1.76 (1H), 1.50-1.63 (8H), 1.28-1.44 (8H); $^{13}$CNMR (150 MHz): δ 154.3, 98.9, 89.9, 72.9, 67.6, 62.3, 52.5, 30.8, 29.7, 29.2, 28.9, 28.7, 27.5, 26.2, 25.5, 19.7, 18.6; FTIR: 2932, 2856, 2236, 1714, 1434, 1249, 1075, 1023, 752 cm$^{-1}$; HRMS-ESI: calc. for $C_{17}H_{28}NaO_4$ (M+Na)$^+$: 319.1885; found: 319.1887.

Step 3

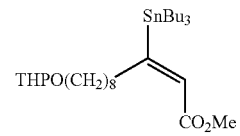

(E)-methyl 11-((tetrahydro-2H-pyran-2-yl)oxy)-3-(tributylstannyl)undec-2-enoate

To a flame-dried round-bottomed flask equipped with two dropping funnels was added iPr$_2$NH (2.5 equiv, 71.4 mmol, 7.22 g, 10.0 mL) and THF (225 mL) and the solution was cooled to 0° C. nBuLi (2.5 equiv, 71.4 mmol, 44.6 mL of a nominally 1.6 M solution in hexanes) was added dropwise and the reaction was stirred for 30 min at 0° C. nBu$_3$SnH (2.3 equiv, 65.6 mmol, 19.1 g, 17.7 mL) was added dropwise and the reaction was stirred for 30 min at 0° C. The reaction was cooled to −50° C. by the controlled addition of dry ice to acetone and CuCN (2.3 equiv, 65.6 mmol, 5.88 g) was added in one portion. The reaction was stirred for 45 min at −50° C. then cooled to −78° C. MeOH (1.70 mL) was added followed by the addition of methyl-11-[(tetrahydro-2H-pyran-2-yl)oxy]-undecynoate (1 equiv, 28.5 mmol, 8.46 g) in THF (85 mL) in one portion. The reaction was stirred at −78° C. for 10 min, then quenched with 170 mL of aq. NH$_4$Cl/NH$_4$OH (pH∼8) and diluted with 150 mL Et$_2$O. The reaction was warmed to rt (orange color is discharged and solution turns colorless), the layers were separated, and the aqueous layer extracted with Et$_2$O (3×120 mL). The combined organic layers were washed with aq. NH$_4$Cl/NH$_4$OH (pH∼8) (100 mL), and brine (120 mL), dried with Na$_2$SO$_4$, concentrated in vacuo, and purified by flash column chromatography (step gradient, Hex to 5% EtOAc/Hex) to afford (E)-methyl 11-((tetrahydro-2H-pyran-2-yl)oxy)-3-(tributylstannyl)undec-2-enoate (15.1 g, 25.5 mmol, 90%). TLC R$_f$=0.30 (5% EtOAc/Hex); $^1$HNMR (500 MHz): δ 5.86-6.03 (m, 1H), 4.56-4.62 (m, 1H), 3.85-3.92 (m, 1H), 3.74 (dt, 1H, J$_1$=9.6 Hz, J$_2$=6.9 Hz), 3.70 (s, 3H), 3.47-3.54 (m, 1H), 3.39 (dt, 1H, J$_1$=9.6 Hz, J$_2$=6.7 Hz), 2.78-2.97 (m, 2H). 1.79-1.90 (1H), 1.69-1.77 (1H), 1.27-1.65 (29H), 0.93-0.99 (5H), 0.91 (t, 9H, J=7.3 Hz); $^{13}$CNMR (125 MHz): δ 174.9, 164.6, 127.0, 98.8, 67.7, 62.3, 50.8, 35.3, 30.8, 29.8, 29.77, 29.68, 29.5, 29.0, 27.4, 26.3, 25.5, 19.7, 13.7, 10.0; FTIR: 2918, 2852, 1717, 1591, 1456, 1431, 1351, 1189, 1162, 1136, 1121, 1077, 1022, 867 cm$^{-1}$; HRMS-ESI: calc. for $C_{29}H_{56}NaO_4Sn$ (M+Na)$^+$: 611.3104; found: 611.3111.

Step 4

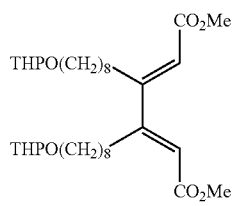

(2E,4E)-dimethyl 3,4-bis(8-((tetrahydro-2H-pyran-2-yl)oxy)octyl)hexa-2,4-dienedioate To a flamed-dried round-bottomed flask was added (E)-methyl 11-((tetrahydro-2H-pyran-2-yl)oxy)-3-(tributylstannyl)undec-2-enoate (1 equiv, 25.5 mmol, 15.0 g), DMF (30 mL), and CuCl (3 equiv, 76.5 mmol, 7.57 g). The reaction was stirred for 3 h at rt, quenched with aq. NH$_4$Cl/NH$_4$OH (pH~8) (35 mL), and stirred for 2 h open to the air. The solution was diluted with H$_2$O (50 mL) and Et$_2$O (50 mL). The layers are separated and the aqueous layer was extracted with Et$_2$O (2×50 mL). The combined organic layers were washed with brine (75 mL), dried with MgSO$_4$, concentrated in vacuo, and purified by flash chromatography (step gradient, 10% EtOAc/Hex to 15% EtOAc/Hex) to afford (2E,4E)-dimethyl 3,4-bis(8-((tetrahydro-2H-pyran-2-yl)oxy)octyl)hexa-2,4-dienedioate (6.27 g, 10.5 mmol, 83%). TLC R$_f$=0.19 (10% EtOAc/Hex); $^1$HNMR (500 MHz): δ 5.84 (bs, 2H), 4.55-4.61 (2H), 3.83-3.92 (2H), 3.69-3.77 (s plus ovlp. m, 8H), 3.47-3.55 (m, 2H), 3.38 (dt, 2H, J$_1$=9.6 Hz, J$_2$=6.7 Hz), 2.72-2.84 (4H), 1.78-1.89 (2H), 1.69-1.76 (2H), 1.50-1.63 (12H), 1.28-1.41 (20H); $^{13}$CNMR (125 MHz): δ 166.5, 161.8, 117.6, 98.8, 67.7, 62.3, 51.2, 30.8, 29.7, 29.6, 29.4, 29.3, 29.1, 28.7, 26.2, 25.5, 19.7; FTIR: 2927, 2855, 1718, 1628, 1433, 1351, 1193, 1163, 1136, 1078, 1023, 986, 905, 868, 814 cm$^{-1}$; HRMS-ESI: calc. for C$_{34}$H$_{58}$NaO$_8$ (M+Na)$^+$: 617.4029; found: 617.4039.

Step 5

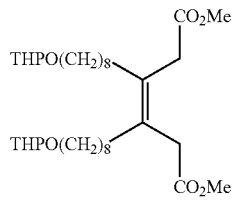

Dimethyl 3,4-bis(8-((tetrahydro-2H-pyran-2-yl)oxy)octyl)hex-3-enedioate

A flame-dried round-bottomed flask was charged with Mg$^o$ (15 equiv, 18.75 mmol, 456 mg) and equipped with a condenser. (2E,4E)-dimethyl 3,4-bis(8-((tetrahydro-2H-pyran-2-yl)oxy)octyl)hexa-2,4-dienedioate (1 equiv, 744 mg, 1.25 mmol) was added in MeOH (16 mL) and the reaction was stirred at rt. After ~30 min, the reaction began refluxing and was left to reflux for ~45 min upon which time the reaction was permitted to cool to rt., quenched with sat. aq. NH$_4$Cl (5 mL), diluted with Et$_2$O (15 mL), and H$_2$O (20 mL). The liquid was decanted into a separatory funnel and the remaining solid was washed several times with Et$_2$O. The layers were separated and the aqueous layer extracted with Et$_2$O (3×20 mL). The combined organic layers were washed with brine (30 mL), dried with Na$_2$SO$_4$ and concentrated in vacuo to afford Dimethyl 3,4-bis(8-((tetrahydro-2H-pyran-2-yl)oxy)octyl)hex-3-enedioate (565 mg crude mass, ~90% pure by $^1$HNMR, 0.95 mmol, 76%) as an inseparable 2:1 mixture of isomers which was used in the next reaction without further purification. TLC R$_f$=0.41 (20% EtOAc/Hex); $^1$HNMR (500 MHz): δ 4.61-4.56 (2H), 3.91-3.85 (2H), 3.77-3.70 (2H), 3.67 (s, 4H), 3.66 (s, 2H), 3.54-3.47 (2H), 3.42-3.35 (2H), 3.12 (s, 2.7H), 3.11 (s, 1.3H), 2.16-2.07 (4H), 1.90-1.80 (2H), 1.76-1.69 (2H), 1.63-1.49 (12H), 1.40-1.24 (20H); $^{13}$CNMR (125 MHz): δ 172.4, 172.2, 130.7, 130.6, 98.9, 67.7, 62.4, 51.8, 37.6, 37.2, 33.3, 32.9, 30.8, 29.8, 29.71, 29.68, 29.49, 29.47, 28.3, 28.1, 26.2, 25.5, 19.7; FTIR: 2926, 2854, 1737, 1434, 1295, 1200, 1156, 1136, 1119, 1078, 1022, 988, 869, 814 cm$^{-1}$; HRMS-ESI: calc. for C$_{34}$H$_{60}$NaO$_8$ (M+Na)$^+$: 619.4186; found: 619.4174.

Step 6

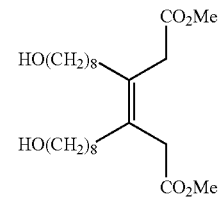

Dimethyl 3,4-bis(8-hydroxyoctyl)hex-3-enedioate

A flamed-dried 20 mL vial fitted with screw-cap septa was charged with Dimethyl 3,4-bis(8-((tetrahydro-2H-pyran-2-yl)oxy)octyl)hex-3-enedioate (1 equiv, 0.855 mmol, 510 mg), MeOH (10 mL) and PTSA (0.1 equiv, 0.086 mmol, 16.4 mg). The reaction was stirred at rt for 14 h, quenched with sat. aq. NaHCO$_3$, and diluted with CH$_2$Cl$_2$ (20 mL) and H$_2$O (10 mL). The layers were separated and the aqueous layer was extracted with CH$_2$Cl$_2$ (2×20 mL). The combined organic layers were washed with H$_2$O (20 mL), dried with Na$_2$SO$_4$, concentrated in vacuo, and purified by flash chromatography (65% EtOAc/Hex) to afford Dimethyl 3,4-bis(8-hydroxyoctyl)hex-3-enedioate (321 mg, 0.75 mmol, 88%) as an inseparable 2:1 mixture of isomers. TLC R$_f$=0.19 (50% EtOAc/Hex); $^1$HNMR (500 MHz): δ 3.61-3.70 (t plus two ovlp. s, 10H, J=6.7 Hz), 3.13 (s, 2.7H), 3.11 (s, 1.3H), 2.07-2.18 (4H), 1.57 (quint., 4H, J=7.8 Hz), 1.49 (bs, 2H), 1.26-1.40 (20H); $^{13}$CNMR (125 MHz): δ 174.4, 174.3, 130.7, 130.6, 62.99, 51.8, 37.6, 37.2, 33.2, 32.82, 32.75, 29.6, 29.5, 29.44, 29.35, 29.32, 28.3, 28.0, 25.71, 25.68; FTIR: 3375, 2926, 2854, 1736, 1434, 1332, 1242, 1192, 1155, 1048 cm$^{-1}$; HRMS-ESI: calc. for C$_{24}$H$_{44}$NaO$_6$ (M+Na)$^+$: 451.3036; found: 451.3022.

Step 7

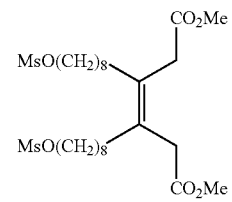

Dimethyl 3,4-bis(8-((methylsulfonyl)oxy)octyl)hex-3-enedioate

To a flamed-dried 20 mL vial fitted with a screw-cap septa was added Dimethyl 3,4-bis(8-hydroxyoctyl)hex-3-enedioate (1 equiv, 0.642 mmol, 275 mg), CH$_2$Cl$_2$ (6 mL), and Et$_3$N (4 equiv, 2.57 mmol, 0.36 mL). The mixture was cooled to 0° C. and DMAP (0.1 equiv, 0.064 mmol, ~8 mg) was added followed by the dropwise addition of MsCl (3 equiv, 1.93 mmol, 0.15 mL). The reaction was allowed to come to ambient temperature over 14 h at which time the reaction was quenched with sat. aq. NaHCO$_3$ (10 mL). The layers were separated and the aqueous layer was extracted with CH$_2$Cl$_2$ (3×15 mL). The combined organic layers were washed with H$_2$O (20 mL), dried with Na$_2$SO$_4$, concentrated in vacuo, and purified by flash column chromatography (45% EtOAc/Hex) to afford Dimethyl 3,4-bis(8-((methylsulfonyl)oxy)octyl)hex-3-enedioate (309 mg, 0.526 mmol, 82%) as an inseparable 2:1 mixture of isomers. TLC R$_f$=0.24 (45% EtOAc/Hex); $^1$HNMR (500 MHz): δ 4.20-4.25 (ovlp. t's, 4H), 3.68 (s, 4H), 3.66 (s, 2H), 2.13 (s, 2.7H), 3.11 (s, 1.3H), 3.02 (s, 6H), 2.07-2.17 (4H), 1.71-1.79 (4H), 1.25-1.45 (20H); $^{13}$CNMR (125 MHz): δ 172.3, 172.2, 130.7, 130.6, 70.20, 70.18, 51.8, 37.6, 37.4, 37.2, 33.2, 32.8, 31.6, 29.58, 29.55, 29.33, 29.29, 29.1, 29.00, 28.97, 28.3, 28.0, 25.4; FTIR: 2929, 2855, 1732, 1435, 1350, 1170, 972, 935, 833, 721 cm$^{-1}$; HRMS-ESI: calc. for C$_{36}$H$_{48}$NaO$_{10}$S$_2$ (M+Na)$^+$: 607.2587; found: 607.2570.

Step 8

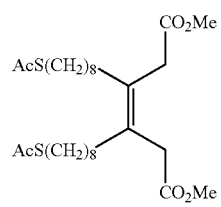

Dimethyl 3,4-bis(8-(acetylthio)octyl)hex-3-enedioate

To a flamed-dried 20 mL vial fitted with a screw-cap septa was added Dimethyl 3,4-bis(8-((methylsulfonyl)oxy)octyl)hex-3-enedioate (1 equiv, 0.46 mmol, 269 mg) and DMF (4 mL). The solution was cooled to 0° C. and KSAc (4 equiv, 1.84 mmol, 210 mg) was added. The reaction was allowed to come to ambient temperature over 15 h then diluted with Et$_2$O (25 mL) and H$_2$O (10 mL). The layers were separated and the organic layer was washed with sat. aq. NaHCO$_3$ (3×10 mL), dried with Na$_2$SO$_4$, concentrated in vacuo, and purified by flash column chromatography (15% EtOAc/Hex) to afford Dimethyl 3,4-bis(8-(acetylthio)octyl)hex-3-enedioate (223 mg, 0.405 mmol, 89%) as an inseparable 2:1 mixture of isomers (Note: partial separation could be achieved, however, both isomers were carried on to the next step). TLC R$_f$=0.43 and 0.38 (20% EtOAc/Hex); $^1$HNMR (500 MHz): δ 3.68 (s, 4H), 3.66 (s, 2H), 3.12 (s, 2.7H), 3.11 (1.3H), 2.84-2.90 (ovlp. t's, 4H), 2.34 (s, 6H), 2.07-2.16 (4H), 1.52-1.61 (4H), 1.19-1.40 (20H); $^{13}$CNMR (125 MHz): δ 196.1, 127.4, 172.2, 130.7, 130.6, 51.8, 37.6, 37.2, 33.3, 32.8, 30.7, 29.7, 29.6, 29.5, 29.38, 29.36, 29.13, 29.09, 29.07, 28.80, 28.78, 28.3, 28.0; FTIR: 2924, 2850, 1733, 1691, 1431, 1338, 1190, 1153, 1134, 995, 951, 722 cm$^{-1}$; HRMS-ESI: calc. for C$_{28}$H$_{48}$NaO$_6$S$_2$ (M+Na)$^+$: 567.2790; found: 567.2770.

Step 9

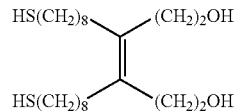

(Z)-3,4-bis(8-mercaptooctyl)hex-3-ene-1,6-diol

To a flamed-dried 20 mL vial fitted with a screw-cap septa was added Dimethyl 3,4-bis(8-(acetylthio)octyl)hex-3-enedioate (1 equiv, 0.36 mmol, 196 mg) and THF (4.5 mL). DIBAl—H (12 equiv, 4.3 mmol, 2.9 mL of a nominally 1.5 M solution in toluene) was added dropwise at rt. The reaction was stirred at rt for 2 h and quenched by the careful addition of 2N HCl (3 mL). The solution was transferred to a seperatory funnel and diluted with sat. aq. NH$_4$Cl (15 mL) and Et$_2$O (15 mL). The layers were separated and the aqueous layer extracted with Et$_2$O (2×15 mL). The combined organic layers were washed with brine (20 mL), dried with Na$_2$SO$_4$, concentrated in vacuo, and purified by flash column chromatography (40% EtOAc/Hex) to afford (Z)-3,4-bis(8-mercaptooctyl)hex-3-ene-1,6-diol (82.8 mg, 0.205 mmol, 57%). TLC R$_f$=0.41 (50% EtOAc/Hex); Mp=67.4-68.2° C.; $^1$HNMR (600 MHz): δ 3.64 (t, 4H, J=6.9 Hz), 2.54 (q, 4H, J=7.4 Hz), 2.35 (t, 4H, J=7.0 Hz), 2.08-2.02 (4H), 1.68 (bs, 2H), 1.62 (quint., 4H, J=7.4 Hz), 1.42-1.27 (22H); $^{13}$CNMR (150 MHz): δ 132.4, 61.3, 34.6, 34.0, 31.7, 29.7, 29.5, 29.2, 29.0, 28.3, 24.6; FTIR: 3402, 3349, 2923, 2850, 1465, 1348, 1028, 721 cm$^{-1}$; HRMS-ESI: calc. for C$_{22}$H$_{44}$NaO$_2$S$_2$ (M+Na)$^+$: 427.2680; found: 427.2679.

Example 4

His-Tagged Methylene Blue Peptide Immobilized on Imidazole-Ni-Modified SAM

Materials 1-(11-mercaptoundecyl)imidazole, 8-mercapto-1-octanol, sulfuric acid (95%), sodium chloride, monosodium phosphate, disodium phosphate, nickel (II) chloride, imidazole, and ethylenediaminetetraacetic acid (EDTA) were purchased from Sigma-Aldrich (St. Louis, Mo.) and used as received without further purification. Diamond suspension (0.1 μm) was purchased from Buehler (Lake Bluff, Ill.). Methylene blue histidine-tagged peptide: (His$_6$-MB) (His-His-His-His-His-His-Lys-Methylene blue) was purchased from Xaia Custom Peptides (Göteborg, Sweden).

All solutions were prepared with deionized water and purified through a Millipore Synergy system (18.2 MΩ·cm, Millipore, Bedford, Mass.). The phosphate buffer saline (PBS) used in this study contained 8.02 mM Na$_2$HPO$_4$, 1.98 mM NaH$_2$PO$_4$, and 100 mM NaCl (pH 7.4).

Instrumentation

Electrochemical measurements were performed at room temperature (22±1° C.) using a CHI 1040A Electrochemical Workstation (CH instruments, Austin, Tex.). Polycrystalline gold disk electrodes with a geometric area of 0.0314 cm$^2$ were purchased from CH instruments (Austin, Tex.). The counter electrode (platinum wire electrode) and the reference electrode (Ag/AgCl; 3M KCl) were also purchased from CH Instruments.

Procedure

Gold electrodes were primed by polishing with a 0.1 µm diamond suspension, rinsing with deionized water and sonicating in a low power sonicator for about five minutes to remove bound particulates. The electrodes were electrochemically cleaned by a series of oxidation and reduction cycles in 0.5 M $H_2SO_4$. The area of each electrode was determined by measuring the charge associated with a gold oxide stripping peak formed after the cleaning process in 0.05 M $H_2SO_4$. After cleaning, the gold disk electrodes were rinsed with deionized water, dried with nitrogen and placed directly in a 100 µM solution of 1-(11-mercaptoundecyl)imidazole in ethanol for 10 minutes. Next, the electrodes were rinsed with ethanol and deionized water and placed in a 2 mM solution of 8-mercapto-1-octanol for 3 hours. The electrodes were then rinsed with ethanol and deionized water.

After formation of the self-assembled monolayer (SAM), electrodes containing the SAM were placed in a solution of $NiCl_2$ (100 mM) in PBS supplemented with EDTA (1 mM) for 30 minutes. The electrodes were then rinsed with deionized water and histidine-tagged methylene blue ($His_6$-MB) (10-15 µL of 5 µM solution in PBS) was dropcasted onto the electrodes for 1 hour. The electrodes were then rinsed thoroughly by washing with deionized water (1×5 mL), ethanol (1×2 mL), deionized water (1×5 mL), 1 M NaCl (1 M, 1×2 mL), and deionized water (1×5 mL)

FIG. 1 is a schematic, depicting the immobilization of $His_6$MB onto the imidazole-Ni SAM prepared in this example. As shown in FIG. 1, 1-(11-mercaptoundecyl)imidazole is immobilized on a gold electrode surface via a thiol-gold bond. In the presence of a divalent cation, such as Ni(II), the imidazole chelating agent can efficiently capture $His_6$-MB.

The $His_6$-MB-bound electrodes were placed in an electrochemical cell containing PBS and analysed by alternating current voltammetry (ACV). AC voltammograms were recorded from −0.05 V to −0.45 V vs. Ag/AgCl at 10 Hz and with an AC amplitude of 25 mV. The electrodes were equilibrated in PBS until a stable methylene blue peak current was obtained. In the displacement step, captured $His_6$-MB was displaced from the SAM by adding a high concentration of free imidazole (250 mM in PBS) to the electrochemical cell. The methylene blue peak current was then monitored for 20-25 minutes. After displacement, the electrochemical cell was rinsed with deionized water and placed in a fresh aliquot of PBS for electrode re-equilibration. AC voltammograms were collected after the monolayer had equilibrated to achieve a stable methylene blue peak current.

In the replacement step, $His_6$-MB was reintroduced to the SAM construct by incubating the electrodes in a new aliquot of $NiCl_2$ (100 mM in PBS) and EDTA (1 mM) for 30 minutes. The electrodes were then rinsed with deionized water and $His_6$-MB (10-15 µL of a 5 µM solution in PBS) was dropcasted onto the electrodes for 1 hour. The electrodes were then rinsed thoroughly by washing with deionized water (1×5 mL), ethanol (1×2 mL), deionized water (1×5 mL), 1 M NaCl (1 M, 1×2 mL), and deionized water (1×5 mL). The electrodes were subsequently placed in a fresh aliquot of PBS. AC voltammograms were collected after the monolayer had equilibrated to achieve a stable methylene blue peak current.

Figure 2:
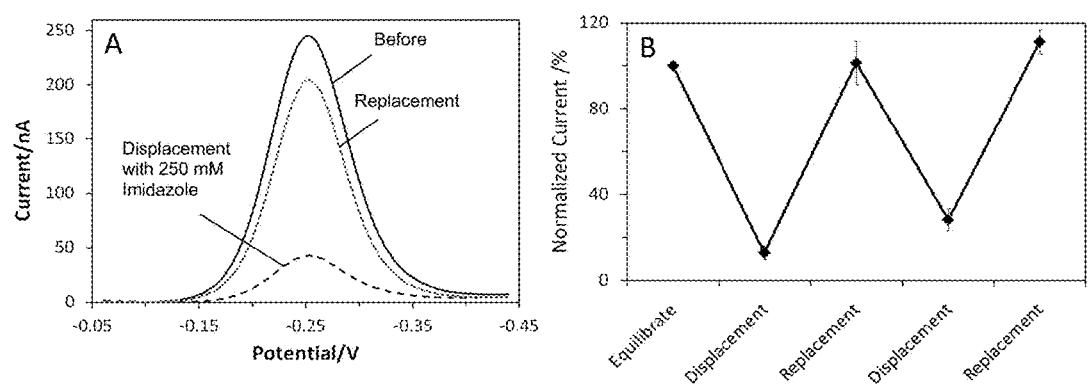
FIG. 2 depicts (A) alternating current voltammograms (ACVs) of $His_6$-MB immobilized on an imidazole-Ni SAM before and after displacement by free imidazole; and (B) a representative displacement/replacement plot for a $His_6$-MB SAM.

FIG. 2A shows ACV data for $His_6$-MB immobilized on an imidazole-Ni SAM before and after displacement by free imidazole. FIG. 2B illustrates the displacement-replacement profile obtained during the experiment. As shown in FIG. 2B, the monolayer of the invention is very stable and can sustain two distinct displacement and replacement cycles without substantial changes in the capacitance current.

Example 5

Electrochemical Biosensor for Detecting Anti-Peanut Antibody (IgY)

In this example, the imidazole-SAM prepared in Example 4 was used in an electrochemical peptide-based sensor for direct detection of an anti-peanut allergen antibody (Igy) using a His-tagged peptide epitope from Arah2, a major peanut allergen ($His_6$-Arah2-10-MB) (His-His-His-His-His-His-Ser-Glu-Asp-Pro-Tyr-Ser-Pro-Ser-Pro-Tyr-Lys-Methylene blue, purchased from Xaia Custom Peptides, Göteborg, Sweden). The antibody target, IgY-APP-3, was purchased from Gallus Immunotech Inc. (Ontario, Canada). IgY-APP-3 antibodies were obtained from hen eggs immunized with *Arachis hypogaea* protein extract.

Gold electrodes containing the imidazole-SAM were placed in a solution of $NiCl_2$ (100 mM) in PBS supplemented with EDTA (1 mM) for 30 minutes. The electrodes were then rinsed with deionized water and histidine-tagged Arah2-10-MB (10-15 µL of 5 µM solution in PBS) was dropcasted onto the electrodes for 1 hour. The electrodes were then rinsed thoroughly by washing with deionized water (1×5 mL), ethanol (1×2 mL), deionized water (1×5 mL), 1 M NaCl (1 M, 1×2 mL), and deionized water (1×5 mL)

The $His_6$-Arah2-10-MB -bound electrodes were placed in an electrochemical cell containing PBS and analysed by alternating current voltammetry (ACV). AC voltammograms were recorded from −0.05 V to −0.45 V vs. Ag/AgCl at 10 Hz and with an AC amplitude of 25 mV. The electrodes were equilibrated in PBS until a stable methylene blue peak current was obtained. Antibodies against *Arachis hypogaea* protein extract (IgY-APP-3) were added consecutively in the following concentrations: 0.5, 1, 10, 20, 30, 40, and 50 nM.

Figure 3:
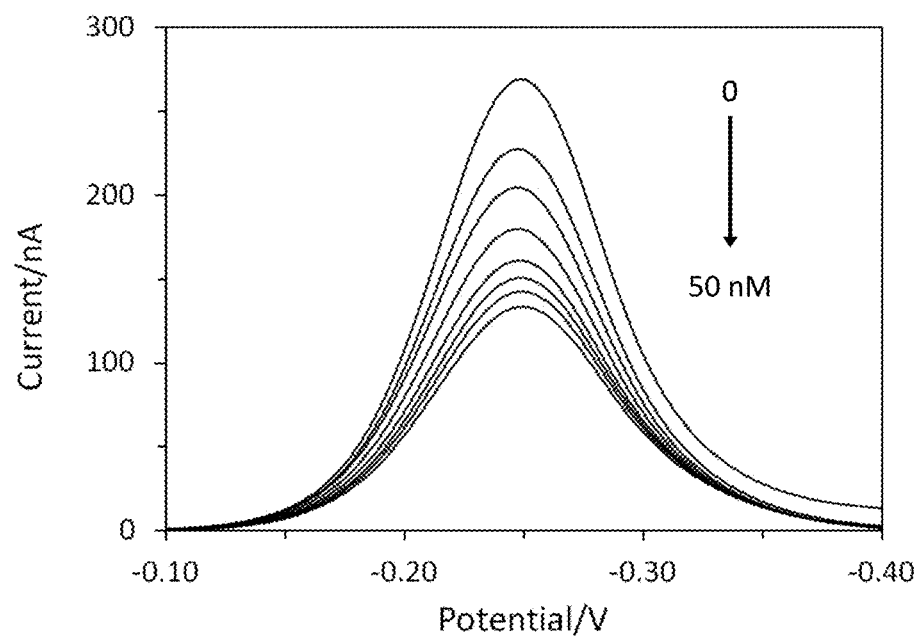
FIG. 3 depicts ACVs of a His$_6$-MB peptide-bound SAM in the presence of varying concentrations of anti-peanut IgY.

FIG. 3 shows ACV data for $His_6$-Arah2-10-MB immobilized on the imidazole-Ni SAM in the absence and presence of various concentrations of the anti-peanut IgY. As shown in FIG. 3, a large MB reduction peak is present, indicating successful immobilization of the His-tagged peptide probe. The sensor responds to the target antibody in a concentration dependent manner, exhibiting an experimental detection limit of 500 mM. Control experiments further suggest that the binding is specific since negligible cross reactivity is observed when the sensor was interrogated with random IgY (data not shown).

Example 6

His-Tagged Methylene Blue Immobilized on Imidazole-Co and Imidazole-Zn Modified SAM In this example, 1 imidazole-Co and imidazole-Zn SAM constructs were prepared and analysed by ACV. Specifically, 1-(11-mercaptoundecyl)imidazole was immobilized on a gold electrode as set forth in Example 4. After formation of the SAM, electrodes containing the SAM were placed in a solution of $ZnCl_2$ (or $CoCl_2$) (100 mM) in PBS supplemented with EDTA (1 mM) for 1 hour. The electrodes were then rinsed with deionized water and histidine-tagged methylene blue ($His_6$-MB) (10-15 µL of 5 µM solution in PBS) was dropcasted onto the electrodes for 1 hour. The electrodes were then rinsed thoroughly by washing with deionized water (1×5 mL), ethanol (1×2 mL), deionized water (1×5 mL), 1 M NaCl (1 M, 1×2 mL), and deionized water (1×5 mL).

The electrodes were placed in an electrochemical cell containing PBS and analysed by ACV. AC voltammograms were recorded from −0.05 V to −0.45 V vs. Ag/AgCl at 10 Hz and with an AC amplitude of 25 mV. The electrodes were equilibrated in PBS until a stable methylene blue peak current was obtained. In the displacement step, captured $His_6$-MB was displaced from the SAM by adding a high concentration of free imidazole (250 mM in PBS) to the electrochemical cell. The methylene blue peak current was then monitored for 20-25 minutes. After displacement, the electrochemical cell was rinsed with deionized water and placed in a fresh aliquot of PBS for electrode re-equilibration. AC voltammograms were collected after the monolayer had equilibrated to achieve a stable methylene blue peak current.

In the replacement step, $His_6$-MB was reintroduced to the SAM construct by incubating the electrodes in a new aliquot of $ZnCl_2$ (or $CoCl_2$) (100 mM in PBS) and EDTA (1 mM) for 1 hour. The electrodes were then rinsed with deionized water and $His_6$-MB (10-15 µL of a 5 µM solution in PBS) was dropcasted onto the electrodes for 1 hour. The electrodes were then rinsed thoroughly by washing with deionized water (1×5 mL), ethanol (1×2 mL), deionized water (1×5 mL), 1 M NaCl (1 M, 1×2 mL), and deionized water (1×5 mL). The electrodes were subsequently placed in a fresh aliquot of PBS. AC voltammograms were collected after the monolayer had equilibrated to achieve a stable methylene blue peak current.

Figure 4:
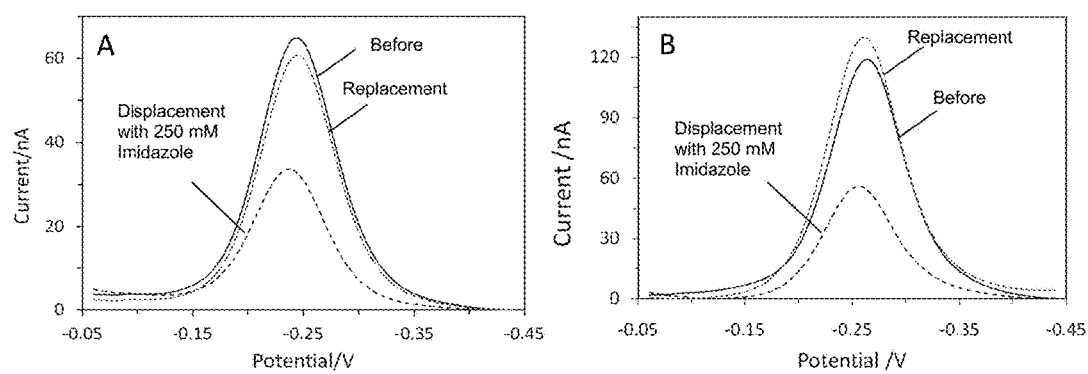
FIG. 4 depicts ACVs of (A) His$_6$-MB immobilized on an imidazole-Co SAM before and after displacement by free imidazole; and (B) His$_6$-MB immobilized on an imidazole-Zn SAM before and after displacement by free imidazole.

FIG. 4A shows ACV data for $His_6$-MB immobilized on an imidazole-Zn SAM before and after displacement by free imidazole. FIG. 4B illustrates ACV data for $His_6$-MB immobilized on an imidazole-Co SAM before and after displacement by free imidazole. As illustrated in this experiment, both Co(II) and Zn(II) are suitable for immobilization of the surrogate probe, $His_6$-MB.

Example 7

Displacement of His-Tagged Methylene Blue From SAM Construct Using Histamine and Histidine In this example, the capacity of histidine and histamine to displace $His_6$-MB from the SAM constructs of the invention was tested. 1-(11-mercaptoundecyl)imidazole was immobilized on a gold electrode as set forth in Example 4. After formation of the SAM, electrodes containing the SAM were placed in a solution of $NiCl_2$ (100 mM) in PBS supplemented with EDTA (1 mM) for 30 minutes. The electrodes were then rinsed with deionized water and histidine-tagged methylene blue ($His_6$-MB) (10-15 µL of 5 µM solution in PBS) was dropcasted onto the electrodes for 1 hour. The electrodes were then rinsed thoroughly by washing with deionized water (1×5 mL), ethanol (1×2 mL), deionized water (1×5 mL), 1 M NaCl (1 M, 1×2 mL), and deionized water (1×5 mL).

The $His_6$-MB-bound electrodes were placed in an electrochemical cell containing PBS and analysed by alternating current voltammetry (ACV). AC voltammograms were recorded from −0.05 V to −0.45 V vs. Ag/AgCl at 10 Hz and with an AC amplitude of 25 mV. The electrodes were equilibrated in PBS until a stable methylene blue peak current was obtained. In the displacement step, captured $His_6$-MB was displaced from the SAM by adding a high concentration of free L-histidine or histamine (250 mM in PBS) to the electrochemical cell. The methylene blue current was then monitored for 20-25 minutes. After displacement, the electrochemical cell was rinsed with deionized water and placed in a fresh aliquot of PBS for electrode re-equilibration. AC voltammograms were collected after the monolayer had equilibrated to achieve a stable methylene blue peak current.

In the replacement step, $His_6$-MB was reintroduced to the SAM construct by incubating the electrodes in a new aliquot of $NiCl_2$ (100 mM in PBS) and EDTA (1 mM) for 30 minutes. The electrodes were then rinsed with deionized water and $His_6$-MB (10-15 µL of a 5 µM solution in PBS) was dropcasted onto the electrodes for 1 hour. The electrodes were then rinsed thoroughly by washing with deionized water (1×5 mL), ethanol (1×2 mL), deionized water (1×5 mL), 1 M NaCl (1 M, 1×2 mL), and deionized water (1×5 mL). The electrodes were subsequently placed in a fresh aliquot of PBS. AC voltammograms were collected after the monolayer had equilibrated to achieve a stable methylene blue peak current.

Figure 5:
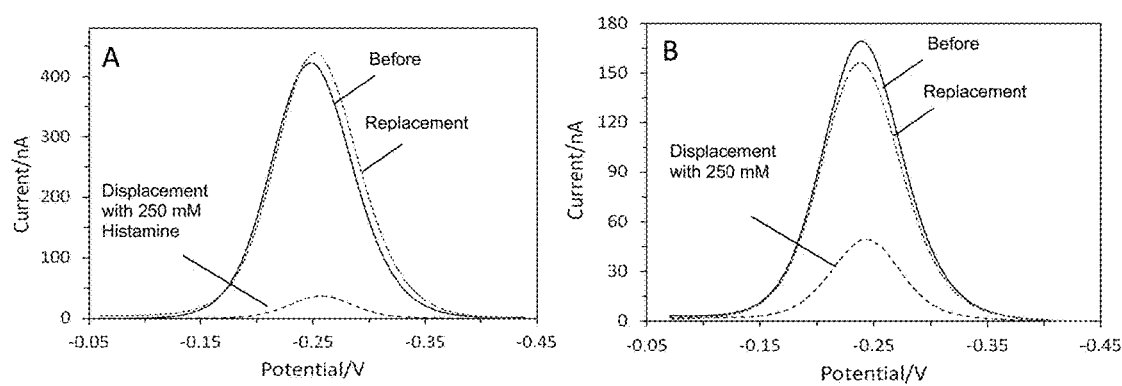
FIG. 5 depicts ACVs of (A) His$_6$-MB immobilized on an imidazole-Ni SAM before and after displacement by free histamine; and (B) His$_6$-MB immobilized on an imidazole-Ni SAM before and after displacement by free histidine.

FIG. 5A shows ACV data for $His_6$-MB immobilized on an imidazole-Ni SAM before and after displacement by histamine, and after replacement with $His_6$-MB. FIG. 4B shows ACV data for $His_6$-MB immobilized on an imidazole-Ni SAM before and after displacement by histidine, and after replacement with $His_6$-MB. As shown, the effectiveness of displacement of $His_6$-MB by histamine is similar to that observed with imidazole. Histidine is also capable of displacing $His_6$-MB from the imidazole-Ni SAM.

Example 8

His-Tagged Methylene Blue Immobilized on a Nitrilotriacetic Acid SAM

Gold electrodes were primed as set forth in Example 4. After cleaning, the gold disk electrodes were rinsed with deionized water, dried with nitrogen and placed directly in a 150 µM solution of 3:7 N—[$N_\alpha$,$N_\alpha$-Bis(carboxymethyl)-L-lysine]-12-mercaptododecanamine (C12-NTA): 8-mercapto-1-octanol (C8-OH) solution in ethanol for 10 minutes. Next, the electrodes were rinsed with ethanol and deionized water and placed in a 2 mM solution of 8-mercapto-1-octanol overnight. The electrodes were then rinsed with ethanol and deionized water.

After formation of the self-assembled monolayer (SAM), electrodes containing the SAM were placed in a solution of $NiCl_2$ (100 mM) in PBS supplemented with EDTA (1 mM) for 30 minutes. The electrodes were then rinsed with deionized water and histidine-tagged methylene blue ($His_6$-MB) (10-15 µL of 5 µM solution in PBS) was dropcasted onto the electrodes for 1 hour. The electrodes were then rinsed thoroughly by washing with deionized water (1×5 mL), ethanol (1×2 mL) and deionized water (1×5 mL). The $His_6$-MB-bound electrodes were placed in an electrochemical cell containing PBS and analysed by alternating current voltammetry (ACV). AC voltammograms were recorded from −0.05 V to −0.45 V vs. Ag/AgCl at 10 Hz and with an AC amplitude of 25 mV. The electrodes were equilibrated in PBS until a stable methylene blue peak current was obtained. In the displacement step, captured $His_6$-MB was displaced from the SAM by adding a high concentration of free imidazole (250 mM in PBS) to the electrochemical cell. The methylene blue peak current was then monitored for 20-25 minutes. After displacement, the electrochemical cell was rinsed with deionized water and placed in a fresh aliquot of PBS for electrode re-equilibration. AC voltammograms were collected after the monolayer had equilibrated to achieve a stable methylene blue peak current.

In the replacement step, His$_6$-MB was reintroduced to the SAM construct by incubating the electrodes in a new aliquot of NiCl$_2$ (100 mM in PBS) and EDTA (1 mM) for 30 minutes. The electrodes were then rinsed with deionized water and His$_6$-MB (10-15 µL of a 5 µM solution in PBS) was dropcasted onto the electrodes for 1 hour. The electrodes were then rinsed thoroughly by washing with deionized water (1×5 mL), ethanol (1×2 mL), deionized water (1×5 mL). The electrodes were subsequently placed in a fresh aliquot of PBS. AC voltammograms were collected after the monolayer had equilibrated to achieve a stable methylene blue peak current.

Figure 6:
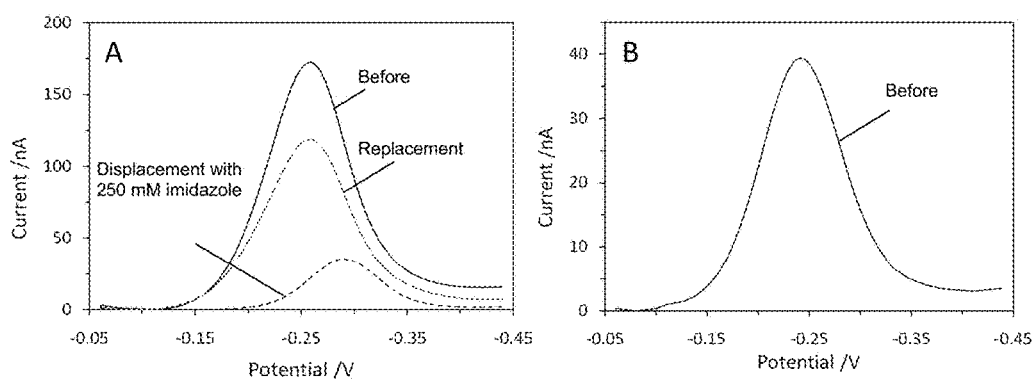
FIG. 6 depicts ACVs of (A) His$_6$-MB immobilized on a nitrolotriacetic acid-Ni SAM before and after displacement by free imidazole; and (B) His$_6$-MB immobilized on a 1,4,7-triazacyclononane-Zn SAM before displacement by free imidazole.

FIG. 6A shows ACV data for His$_6$-MB immobilized on an NTA-Ni SAM before and after displacement by free imidazole. As shown, His$_6$-MB can be successfully immobilized on a NTA-modified monolayer using Ni(II) as the metal ion. It was observed that NTA is a highly effective surface immobilized ligand for probe capture. In the imidazole system, two imidazole head groups are desirable to achieve a stable metal ligand complex, wherease only one NTA ligand is needed for stabilized metal ligand complex formation. The NTA-Ni SAM can also withstand the displacement cycle without significant loss of nickel metal ions, thus a "metal-replacement step" is not necessary. The captured His$_6$-MB probes can be easily displaced by excess amount of imidazole in the solution and the imidazole ligands can be effectively replaced by His$_6$-MB.

Example 9

His-Tagged Methylene Blue Immobilized on a Triazacyclononane SAM

Gold electrodes were primed as set forth in Example 4. After cleaning, the gold disk electrodes were rinsed with deionized water, dried with nitrogen and placed directly in a 100 µM solution of C11-bnTACN solution (premixed with 0.17 mM Tris-(2-carboxymethyl)phosphine hydrochloride in deionized water for 1 hour) in ethanol for 10 minutes. Next, the electrodes were rinsed with ethanol and deionized water and placed in a 2 mM solution of 8-mercapto-1-octanol for 3 hours. The electrodes were then rinsed with ethanol and deionized water.

After formation of the self-assembled monolayer (SAM), electrodes containing the SAM were placed in a solution of ZnCl$_2$ (100 mM) in PBS supplemented with EDTA (1 mM) for 30 minutes. The electrodes were then rinsed with deionized water and histidine-tagged methylene blue (His$_6$-MB) (10-15 µL of 5 µM solution in PBS) was dropcasted onto the electrodes for 1 hour. The electrodes were then rinsed thoroughly by washing with deionized water (1×5 mL), ethanol (1×2 mL) and deionized water (1×5 mL).

The His$_6$-MB-bound electrodes were placed in an electrochemical cell containing PBS and analysed by alternating current voltammetry (ACV). AC voltammograms were recorded from −0.05 V to −0.45 V vs. Ag/AgCl at 10 Hz and with an AC amplitude of 25 mV. The electrodes were equilibrated in PBS until a stable methylene blue peak current was obtained. In the displacement step, captured His$_6$-MB was displaced from the SAM by adding a high concentration of free imidazole (250 mM in PBS) to the electrochemical cell. The methylene blue peak current was then monitored for 20-25 minutes. After displacement, the electrochemical cell was rinsed with deionized water and placed in a fresh aliquot of PBS for electrode re-equilibration. AC voltammograms were collected after the monolayer had equilibrated to achieve a stable methylene blue peak current.

FIG. 6B shows ACV data for His$_6$-MB immobilized on an TACN-Zn SAM. As shown, His$_6$-MB can be successfully immobilized on a TACN-modified monolayer using Zn(II) as the metal ion.

Example 10

Electrochemical Peptide-Based HIV Sensor Fabricated on an NTA-Ni SAM

Materials

HS—(CH$_2$)$_{11}$-EG3-NTA (C11-EG3-NTA) was purchased from ProChimia Surfaces Sp. (Poland). Monocarboxymethylene blue NHS ester (NHS-MB) was purchased from emp Biotech GmbH (Berlin, Germany) and the dialysis bag (1000 MW cut-off) was purchased from Spectrum Labs (Rancho Dominguez, Calif.). The protein probe and target (HIV-1 p24 gag his and HIV-1 p24 antibody) was purchased from ProSpec Bio (Rehovot, Israel) and was reconstituted in PBS at a concentration of 76.9 µM and 6.66 µM respectively.

6-mercapto-1-hexanol (C6-OH), sulphuric acid (95%), hydrochloric acid, HEPES, trizma base, magnesium chloride, potassium chloride, calcium chloride, sodium chloride, monosodium phosphate, disodium phosphate, nickel (II) chloride, imidazole, and ethylenediaminetetraacetic acid (EDTA) were used as received from Sigma-Aldrich (St. Louis, Mo.) without further purification. Diamond suspension, 0.1 µm, was purchased from Buehler (Lake Bluff, Ill.).

All the solutions were made with deionized water (DI H$_2$O), purified through a Millipore Synergy system (18.2 MΩ·cm, Millipore, Bedford, Mass.). The phosphate buffer saline (PBS) used in this study contained 8.02 mM Na$_2$HPO$_4$, 1.98 mM NaH$_2$PO$_4$, 100 mM NaCl, pH 7.4. The Phys2 buffer used in this study contained 20 mM Tris, 140 mM NaCl, 5 mM KCl, 1 mM MgCl$_2$, and 1 mM CaCl$_2$ pH 7.4.

Procedure

HIV-1 P24 proteins (34.2 µM) were modified using a solution of NHS-MB (2.2 mM) in chilled HEPES (6.7 mM, pH 9.5) by mixing the solution and allowing the solution to sit for 90 minutes with a cold pack in the dark. The solution was then dialyzed for 4 hours in HEPES (20 mM, pH 9.5) and transferred to a 10 mM solution of HEPES (pH 7.5) overnight.

Gold electrodes were polished and primed as set forth in Example 4. After cleaning, the gold disk electrodes were rinsed with deionized water, dried with nitrogen and placed directly in a 2 mM solution of 1:3 C11-EG3-NTA:C6-OH in ethanol for 24 hours at 4° C. Next, the electrodes were rinsed with ethanol and deionized water and dried with nitrogen gas.

After formation of the SAM, electrodes containing the SAM were placed in a solution of NiCl$_2$ (100 mM) in Tris-HCL (10 mM, pH 8.0) for 30 minutes. The electrodes were then rinsed with deionized water and HIV-1 P24-MB (10-15 µL of 7.3 µM solution in PBS) was dropcasted onto the electrodes for 1 hour. The electrodes were then rinsed thoroughly by washing with deionized water (1×5 mL), 5% TWEEN 20 (1×2 mL) and deionized water (1×10 mL). The electrodes were then placed in an electrochemical cell containing Phys2 and analysed via alternating current voltammetry (ACV). AC voltammograms were recorded from −0.1 V to −0.4 V vs. Ag/AgCl at 10 Hz and with an AC amplitude of 25 mV. The electrodes were allowed to equilibrate in Phys2 until a stable MB peak current was obtained. The target, 50 nM anti-p24 antibodies were added to the Phys2 buffer and monitored via ACV.

Figure 7:
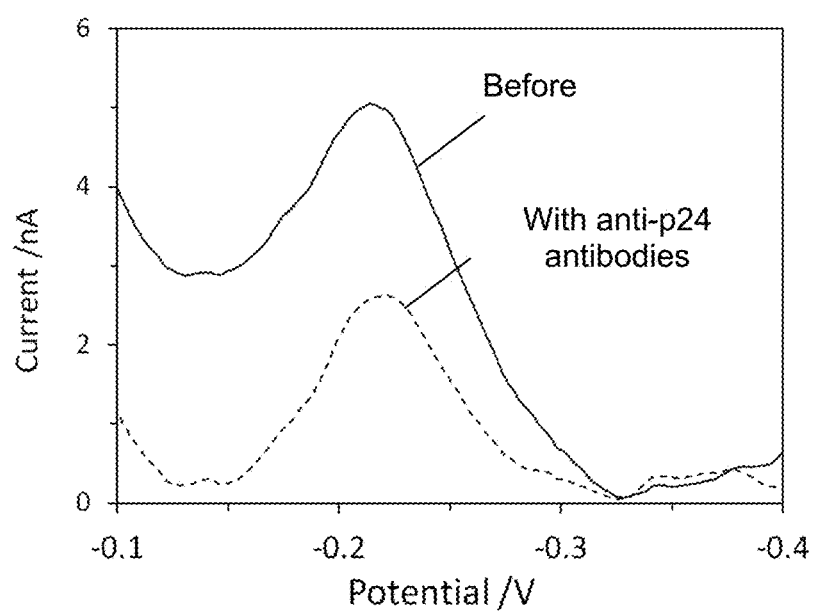
FIG. 7 depicts ACVs of a His$_6$-MB peptide-bound SAM in the absence and presence of anti-p24 antibodies.

FIG. 7 shows ACV data of the sensor prepared in this experiment in the absence and presence of anti-p-24 antibodies. As illustrated in this experiment, His-tagged and MB-modified HIV p24 antigent can be immobilized onto an NTA-Ni SAM of the invention. The MB signal is stable and a small reduction in the MB signal is evident upon addition of the target anti-p24 antibodies.

Example 11

His-Tagged Methylene Blue Immobilized on SAMs Fabricated with C11-Im, dS1-Im and dS2-Im Materials 8-mercapto-1-octanol (C8-OH), sulphuric acid (95%), sodium chloride, monosodium phosphate, disodium phosphate, nickel (II) chloride, trizma base, hydrochloric acid, and ethylenediaminetetraacetic acid (EDTA) were purchased from Sigma-Aldrich (St. Louis, Mo.) and used as received without further purification. Diamond suspension (0.1 μm) was purchased from Buehler (Lake Bluff, Ill.). Methylene blue histidine-tagged peptide: ($His_6$-MB) (His-His-His-His-His-His-Lys-Methylene blue) was purchased from Xaia Custom Peptides (Göteborg, Sweden).

All solutions were prepared with deionized water and purified through a Millipore Synergy system (18.2 MΩ·cm, Millipore, Bedford, Mass.). The phosphate buffer saline (PBS) used in this study contained 8.02 mM $Na_2HPO_4$, 1.98 mM $NaH_2PO_4$, and 100 mM NaCl (pH 7.4).

Instrumentation

Electrochemical measurements were performed at room temperature (22±1° C.) using a CHI 1040A Electrochemical Workstation (CH instruments, Austin, Tex.). Polycrystalline gold disk electrodes with a geometric area of 0.0314 $cm^2$ were purchased from CH instruments (Austin, Tex.). The counter electrode (platinum wire electrode) and the reference electrode (Ag/AgCl; 3M KCl) were also purchased from CH Instruments.

Procedure

Gold electrodes were primed by polishing with a 0.1 μm diamond suspension, rinsing with deionized water and sonicating in a low power sonicator for about five minutes to remove bound particulates. The electrodes were electrochemically cleaned by a series of oxidation and reduction cycles in 0.5 M $H_2SO_4$. The area of each electrode was determined by measuring the charge associated with a gold oxide stripping peak formed after the cleaning process in 0.05 M $H_2SO_4$.

Figure 8:
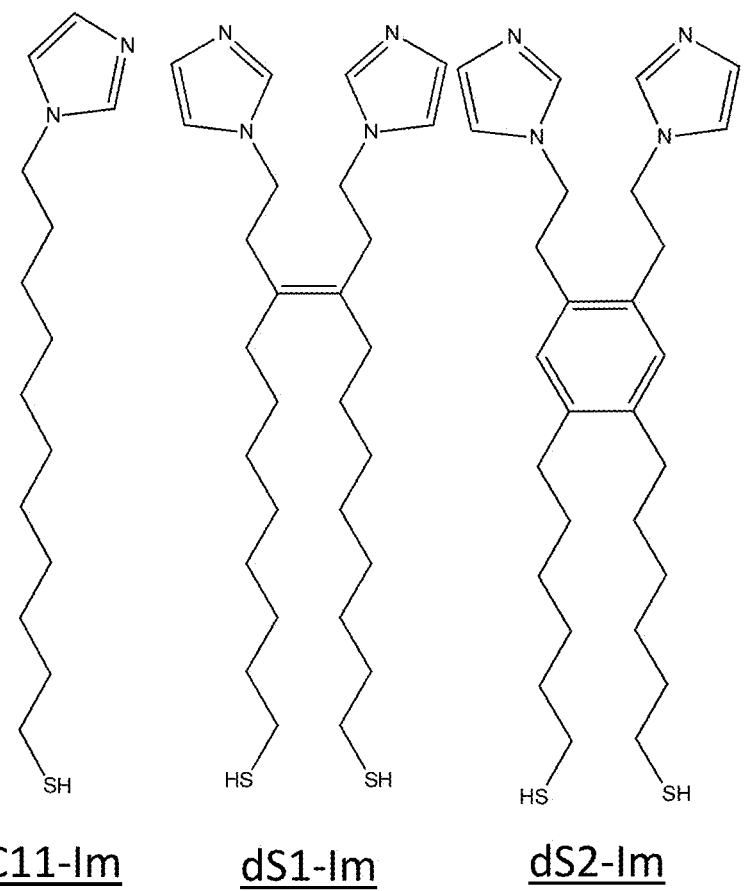
FIG. 8 depicts structures of three imidazole-containing molecules of the invention.

Before fabricating the monolayer, the dS-Im molecules were deprotected by allowing solutions containing the compounds to incubate for 1 hour. Specifically, Solution A was prepared to contain either dS1-Im (1.5 mM) or dS2-Im (1.5 mM) in solution with KOH (90 mM in EtOH). Solution B was made after incubating Solution A for an hour by mixing 100 μL of Solution A with 500 μL of 2 mM C8-OH in DI $H_2O$. FIG. 8 shows the structures for compounds dS1-Im and dS2-Im.

After the cleaning process, the gold disk electrodes were rinsed with deionized water, dried with nitrogen and placed directly in solution B for 3 hours. Next, the electrodes were rinsed with ethanol and deionized water and placed in a solution of $NiCl_2$ (100 mM) in Tris-HCl (10 mM) for 30 minutes. The electrodes were then rinsed with deionized water and histidine-tagged methylene blue ($His_6$-MB) (10-15 μL of 5 μM solution in PBS, pH 8.0) for 1 hour. The electrodes were then rinsed thoroughly with PBS.

The $His_6$-MB-bound electrodes were placed in an electrochemical cell containing PBS and analysed by alternating current voltammetry (ACV). AC voltammograms were recorded from −0.05 V to −0.5 V vs. Ag/AgCl at 10 Hz and with an AC amplitude of 25 mV. The electrodes were equilibrated in PBS until a stable methylene blue peak current was obtained. In the displacement step, captured $His_6$-MB was displaced from the SAM by adding a high concentration of $NiCl_2$ (100 mM in 10 mM Tris-HCl) 250 mM in PBS) to the electrochemical cell. The methylene blue peak current was then monitored for 40 minutes. After displacement, the electrochemical cell was rinsed with deionized water and placed in a fresh aliquot of PBS for electrode re-equilibration. AC voltammograms were collected after the monolayer had equilibrated to achieve a stable methylene blue peak current.

To replace probes that were removed in the displacement step, the electrodes were incubated in a new aliquot of $His_6$-MB (5 μM in PBS pH 8.0) for 1 hour. The electrodes were then rinsed using PBS. The electrodes were subsequently placed in a fresh aliquot of PBS and AC voltammograms were collected after the monolayer had equilibrated to achieve a stable methylene blue peak current.

Figure 9:
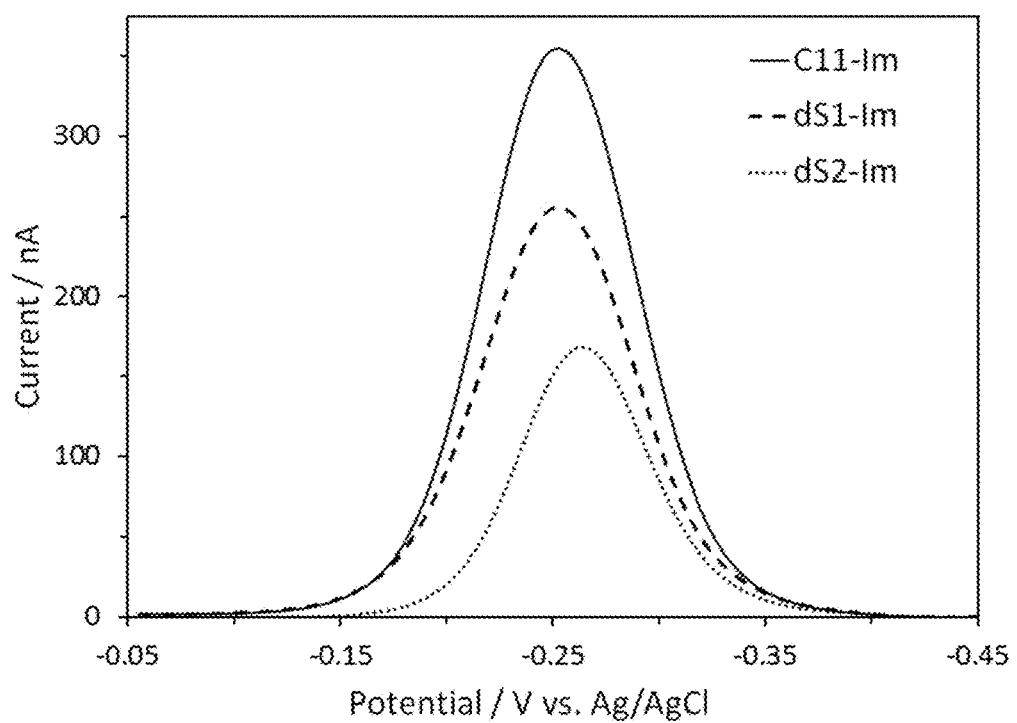
FIG. 9 depicts ACVs of His$_6$-MB immobilized on SAMs fabricated using compounds C11-Im, dS1-Im, and dS2-Im.
Figure 10:
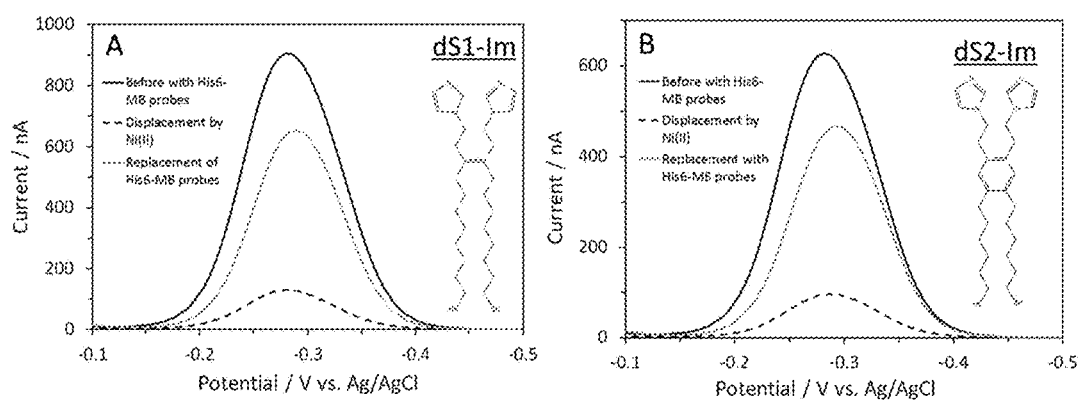
FIG. 10 depicts ACVs of His$_6$-MB modified (A) dS1-Im and (B) dS2-Im SAMs before and after displacement by Ni(II), and after replacement by His$_6$-MB.

The ACV trace of the $His_6$-MB SAM fabricated using C11-Im, dS1-Im, and dS2-Im is shown in FIG. 9. FIG. 10A shows the ACV trace of the $His_6$-MB SAM fabricated dS1-Im, before and after displacement with Ni(II), and after replacement with $His_6$-MB. FIG. 10B shows the ACV trace of the $His_6$-MB SAM fabricated dS2-Im, before and after displacement with Ni(II), and after replacement with $His_6$-MB. As illustrated, the SAMs fabricated in this example can be used to immobilize histidine-modified peptide probes. The immobilized probes can be rapidly displaced by incubating the electrode in a Ni(II) solution. Replacement of the probes can be easily achieved by immersing the electrode in a new peptide probe solution.

Various modifications of the invention, in addition to those described herein, will be apparent to those skilled in the art from the foregoing description. Such modifications are also intended to fall within the scope of the appended claims. Each reference, including patents, patent applications, and publications, cited in the present application is incorporated herein by reference in its entirety.

What is claimed is:

1. A method of detecting a biomolecule of interest in a sample, which comprises the steps of:
(a) providing a monolayer component that comprises a self-assembled monolayer comprising a compound of Formula II:

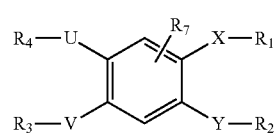

II wherein:
$R_1$-$R_4$ are each, independently, $SR_a$, OH, $COR_b$, heterocyclyl, heteroaryl, CN, $N_3$ or halo;
$R_7$ is 0-2 $R_c$ groups,
X, Y, U, and V are each, independently, $C_{2-6}$alkyl;
$R_a$ is H, $C_{1-20}$alkyl, C(O)H, CO—($C_{1-20}$alkyl), SH, S($C_{1-20}$alkyl);
$R_b$ is $C_{0-20}$hydroxyl, $C_{3-10}$heterocycloalkyl, $C_{5-10}$aryl, $C_{5-10}$heteroaryl, or $NR'R''$;
$R_c$ is alkyl, alkenyl, alkynyl, cycloalkyl, aryl, heteroaryl, hydroxyl, halo, haloalkyl, haloalkoxy, cyano, nitro, azido, amino, alkylamino, dialkylamino, carboxy, carboxyalkyl ester, carboxy aryl ester, aminocarbonyl, alkylaminocarbonyl, dialkylaminocarbonyl, sulfonyl, aminosulfonyl, alkylaminosulfonyl, dislakylaminosulfonyl, arylsulfonyl, arylsulfinyl, alkylsulfonyl, or arylsufonyl; and $R^I$ and $R^{II}$ are each, independently selected from H, substituted or unsubstituted alkyl, or $R^I$ and $R^{II}$ come together to form a 4-10-membered substituted or unsubstituted heterocyclic ring;

(b) binding a multivalent cation to the monolayer;

(c) capturing a binding partner for the biomolecule of interest onto the monolayer, wherein the binding partner comprises a detectable marker and a first moiety capable of binding the multivalent cation;

(d) exposing the sample to the monolayer component; and (e) detecting a signal of detectable marker.

2. The method of claim 1, wherein the self-assembled monolayer comprises a plurality of compounds of Formula II, wherein at least about 5% of the compounds are functionalized with a second moiety capable of binding the multivalent cation.

3. The method of claim 2, wherein the second moiety capable of binding the multivalent cation comprises a chelating molecule.

4. The method according to claim 1, wherein at least one of $R_3$ or $R_4$ comprises a second moiety capable of binding the multivalent cation.

5. The method according to claim 4, wherein the second moiety capable of binding the multivalent cation is a chelating molecule.

6. The method of claim 5, wherein the chelating molecule comprises an imidazole, nitrilotriacetic acid, or 1,4,7-triazacyclononane moiety.

7. The method of claim 5, wherein the chelating molecule is imidazole.

8. The method of claim 5, wherein the chelating molecule is nitrilotriacetic acid.

9. The method of claim 1, wherein the self-assembled monolayer comprises a compound selected from:

6,6'-(4,5-bis(2-(1H-imidazol-1-yl)ethyl)-1,2-phenylene) bis(hexane-1-thiol); and ((4,5-bis(2-(1H-imidazol-1-yl)ethyl)-1,2-phenylene)bis (hexane-6,1-diyl)) diethanethioate.

10. The method of claim 1, wherein the multivalent cation is a divalent or trivalent cation.

11. The method of claim 1, wherein the multivalent cation is a divalent cation.

12. The method of claim 11, wherein the divalent cation is selected from Zn(II), Ni(II), or Co(II).

13. The method of claim 12, wherein the divalent cation is Ni(II).

14. The method of claim 1, wherein the first moiety capable of biding a multivalent cation is a chelating agent.

15. The method of claim 14, wherein the chelating agent comprises one or more amino acids.

16. The method of claim 15, wherein the chelating agent comprises one or more histidine amino acids.

17. The method of claim 16, wherein the chelating agent is a histidine tag.

18. The method of claim 17, wherein the histidine tag is hexahistidine.

19. The method of claim 1, wherein the detectable marker is a redox molecule.

20. The method of claim 19, wherein the redox molecule is methylene blue.

21. The method of claim 1, wherein the binding partner is any ligand capable of binding to the biomolecule.

22. The method of claim 1, wherein the binding partner is a peptide.

23. The method of claim 1, wherein the method further comprises a regeneration step.

24. The method of claim 23, wherein the regeneration comprises displacing the binding partner from the monolayer upon treatment with any reagent capable of biding the multivalent cation.

25. The method of claim 23, wherein the regeneration comprises displacing the binding partner from the monolayer upon treatment with a chelating molecule.

26. The method of claim 1, wherein the method is for detecting ligands such as hormones, antigens or antibodies.

27. The method of claim 26, wherein the method is for detecting and anti-peanut antigen.

28. The method of claim 26, wherein the method is for detecting an anti-HIV-p24 antibody.

* * * * *

UNITED STATES PATENT AND TRADEMARK OFFICE
CERTIFICATE OF CORRECTION

PATENT NO. : 9,829,487 B2  
APPLICATION NO. : 14/798145  
DATED : November 28, 2017  
INVENTOR(S) : Patrick H. Dussault et al.

Page 1 of 1

It is certified that error appears in the above-identified patent and that said Letters Patent is hereby corrected as shown below:

In the Specification

In Column 1 Line 18 please delete "This work was supported in part by the National Science Foundation (NSF Grant EPSCoR RII (2010-2015)). The Government may have certain rights in the invention, as specified by law." and replace it with --This invention was made with government support under EPS1004094 awarded by the National Science Foundation and W911NF-09-2-0039 awarded by Army Research Office. The government has certain rights in the invention.--, therefor.

Signed and Sealed this  
Second Day of January, 2018

Joseph Matal  
*Performing the Functions and Duties of the  
Under Secretary of Commerce for Intellectual Property and  
Director of the United States Patent and Trademark Office*